US007989664B2

(12) United States Patent
Cortright

(10) Patent No.: US 7,989,664 B2
(45) Date of Patent: *Aug. 2, 2011

(54) METHODS AND SYSTEMS FOR GENERATING POLYOLS

(75) Inventor: Randy D. Cortright, Madison, WI (US)

(73) Assignee: Virent Energy Systems, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/834,306

(22) Filed: Jul. 12, 2010

(65) Prior Publication Data

US 2010/0280275 A1 Nov. 4, 2010

Related U.S. Application Data

(63) Continuation of application No. 11/800,671, filed on May 7, 2007, now Pat. No. 7,767,867.

(60) Provisional application No. 60/798,484, filed on May 8, 2006.

(51) Int. Cl.
*C07C 45/85* (2006.01)
*C07C 29/90* (2006.01)
*C07C 29/88* (2006.01)

(52) U.S. Cl. ......... 568/403; 568/840; 568/852; 568/860

(58) Field of Classification Search .................. 568/400, 568/420, 700, 840, 852, 861, 403
See application file for complete search history.

(56) References Cited

U.S. PATENT DOCUMENTS

| | | | |
|---|---|---|---|
| 2,965,679 A | 12/1960 | Conradin et al. |
| 4,223,001 A | 9/1980 | Novotny et al. |
| 4,401,823 A | 8/1983 | Arena |
| 4,476,331 A | 10/1984 | Dubeck et al. |
| 4,496,780 A | 1/1985 | Arena |
| 4,554,260 A | 11/1985 | Pieters et al. |
| 4,642,394 A | 2/1987 | Che |
| 5,019,135 A | 5/1991 | Sealock, Jr. et al. |
| 5,026,927 A | 6/1991 | Andrews et al. |
| 5,139,002 A | 8/1992 | Lynch et al. |
| 5,214,219 A | 5/1993 | Casale et al. |
| 5,306,847 A | 4/1994 | Gehrer et al. |
| 5,326,912 A | 7/1994 | Gubitosa et al. |
| 5,354,914 A | 10/1994 | Gubitosa et al. |
| 5,496,786 A | 3/1996 | Gubitosa et al. |
| 5,543,379 A | 8/1996 | Gubitosa et al. |
| 5,578,647 A | 11/1996 | Li et al. |
| 5,600,028 A | 2/1997 | Gubitosa et al. |
| 5,616,154 A | 4/1997 | Elliott et al. |
| 5,616,817 A | 4/1997 | Schuster et al. |
| 5,651,953 A | 7/1997 | Yokoyama et al. |
| 5,660,602 A | 8/1997 | Collier, Jr. et al. |
| 5,666,923 A | 9/1997 | Collier, Jr. et al. |
| 5,787,864 A | 8/1998 | Collier, Jr. et al. |
| 5,861,137 A | 1/1999 | Edlund |
| 6,059,995 A | 5/2000 | Topsoe et al. |
| 6,152,975 A | 11/2000 | Elliott et al. |
| 6,171,992 B1 | 1/2001 | Autenrieth et al. |
| 6,207,132 B1 | 3/2001 | Lin et al. |
| RE37,329 E | 8/2001 | Gubitosa et al. |
| 6,280,701 B1 | 8/2001 | Autenrieth et al. |
| 6,291,725 B1 | 9/2001 | Chopade et al. |
| 6,361,757 B1 | 3/2002 | Shikada et al. |
| 6,372,680 B1 | 4/2002 | Wu et al. |
| 6,387,554 B1 | 5/2002 | Verykios |
| 6,397,790 B1 | 6/2002 | Collier, Jr. |
| 6,413,449 B1 | 7/2002 | Wieland et al. |
| 6,429,167 B1 | 8/2002 | Maeno et al. |
| 6,440,895 B1 | 8/2002 | Tonkovich et al. |
| 6,479,428 B1 | 11/2002 | Tonkovich et al. |
| 6,479,713 B1 | 11/2002 | Werpy et al. |
| 6,508,209 B1 | 1/2003 | Collier, Jr. |
| 6,570,043 B2 | 5/2003 | Elliott et al. |
| 6,607,707 B2 | 8/2003 | Reichman et al. |
| 6,670,300 B2 | 12/2003 | Werpy et al. |
| 6,677,385 B2 | 1/2004 | Werpy et al. |
| 6,699,457 B2 | 3/2004 | Cortright et al. |
| 6,739,125 B1 | 5/2004 | Mulligan |
| 6,749,828 B1 | 6/2004 | Fukunaga |
| 6,762,149 B2 | 7/2004 | Tonkovich et al. |
| 6,765,101 B1 | 7/2004 | Bhasin et al. |
| 6,841,085 B2 | 1/2005 | Werpy et al. |
| 6,953,873 B2 | 10/2005 | Cortright et al. |
| 6,964,757 B2 | 11/2005 | Cortright et al. |

(Continued)

FOREIGN PATENT DOCUMENTS

WO W003/045851 6/2003

(Continued)

OTHER PUBLICATIONS

Badger, P.C., "Ethanol From Cellulose: A General Review," Ethanol From Cellulose: A General Review (2002).
Bardin, B.B., et al, "Acidity of Keggin-Type Heteropolycompounds Evaluated by Catalytic Probe Reactions, Sorption Microcalorimetry, and Density Functional Quantum Chemical Calculations," J. Phys. Chem. B 102:10817-10825 (1998).
Brown, N.F., et al., "Carbon-Halogen Bond Scission and Rearrangement of Beta-Halohydrins on the Rh(111) Surface," J. Phys. Chem. 98:12737-12745 (1994).
Chen, N.Y., et al., "Liquid Fuel From Carbohydrates," Chemtech Aug. 1986 p. 506-509.

(Continued)

*Primary Examiner* — Sikarl Witherspoon
(74) *Attorney, Agent, or Firm* — Quarles & Brady LLP

(57) ABSTRACT

Disclosed are methods for generating propylene glycol, ethylene glycol and other polyols, diols, ketones, aldehydes, carboxylic acids and alcohols from biomass using hydrogen produced from the biomass. The methods involve reacting a portion of an aqueous stream of a biomass feedstock solution over a catalyst under aqueous phase reforming conditions to produce hydrogen, and then reacting the hydrogen and the aqueous feedstock solution over a catalyst to produce propylene glycol, ethylene glycal and the other polyols, diols, ketones, aldehydes, carboxylic acids and alcohols. The disclosed methods can be run at lower temperatures and pressures, and allows for the production of oxygenated hydrocarbons without the need for hydrogen from an external source.

44 Claims, 9 Drawing Sheets

U.S. PATENT DOCUMENTS

| | | |
|---|---|---|
| 6,964,758 B2 | 11/2005 | Cortright et al. |
| 6,969,506 B2 | 11/2005 | Tonkovich et al. |
| 6,982,328 B2 | 1/2006 | Werpy et al. |
| 7,038,094 B2 | 5/2006 | Werpy et al. |
| 7,186,668 B2 | 3/2007 | Werpy et al. |
| 7,199,250 B2 | 4/2007 | Werpy et al. |
| 7,767,867 B2 | 8/2010 | Cortright et al. |
| 2003/0099593 A1 | 5/2003 | Cortright et al. |
| 2004/0175806 A1 | 9/2004 | Werpy et al. |
| 2005/0064560 A1 | 3/2005 | Werpy et al. |
| 2005/0065337 A1 | 3/2005 | Werpy et al. |
| 2005/0203195 A1 | 9/2005 | Wang et al. |
| 2005/0207971 A1 | 9/2005 | Cortright et al. |
| 2005/0244312 A1 | 11/2005 | Suppes et al. |
| 2005/0244329 A1 | 11/2005 | Casanave et al. |
| 2005/0271579 A1 | 12/2005 | Rogers |
| 2006/0013759 A1 | 1/2006 | Jiang et al. |
| 2007/0123739 A1 | 5/2007 | Crabtree et al. |
| 2007/0135301 A1 | 6/2007 | Holcomb, Jr. |
| 2007/0149830 A1 | 6/2007 | Tuck et al. |
| 2007/0173643 A1 | 7/2007 | Werpy et al. |
| 2007/0173651 A1 | 7/2007 | Holladay et al. |
| 2007/0173652 A1 | 7/2007 | Holladay et al. |
| 2007/0293665 A1 | 12/2007 | Holcomb |

FOREIGN PATENT DOCUMENTS

| | | |
|---|---|---|
| WO | WO 2007/027832 | 3/2007 |
| WO | WO 2007/053705 | 5/2007 |
| WO | WO 2007/075476 | 7/2007 |
| WO | WO 2007/099161 | 9/2007 |

OTHER PUBLICATIONS

Chiu C-W., et al., "Distrbution of Methanol and Catalysts between Biodiesel and Glycerin Phases," AIChE Jounal 51:1274-1278 (2005).

Chiu, C-W., et al., "Removal of Residual Catalyst from Simulated Biodiesel's Crude Glycerol for Glycerol Hydrogenolysis to Propylene Glycol," Ind. Eng. Chem. Res 45:791-795 (2006).

Cortright, R.D., "Hydrogen from catalytic reforming of biomass-derived hydrocarbons in liquid water," Nature 418:964-967 (2002).

Crabtree, S.P., et. al., "Novel Catalysis for Glycol Manufacture".

Dasari M.A., et al.,"Low pressure hydrogenolysis of gycerol to propylene gycol," Applied catalysis A: General 281:225-231 (2005).

Elliott, D.C., et al., "Chemical Processing in High-Pressure Aqueous Environments. 7. Process Development for Catalytic Gasification of Wet Biomass Feedstocks," Ind. Eng. Chem. Res. 43:1999-2004 (2004).

Fraser, J., "Roadmap for Cellulosic Ethanol Production," U.S. Department of Energy, Jun. 2006.

Fukuoka, A., et al., "Catalytic Conversion of Cellulose into Sugar Alcohols," Angew. Chem. Int. Ed. 45:5161-5163 (2006).

Greer, D., "Creating Cellulosic Ethanol: Spinning Straw into Fuel," May 2005 eNews Bulletin.

Huber, G.W., et al., "Raney Ni-Sn Catalyst for H2 Production from Biomass-Derived Hydrocarbons," Science 300:2075-2077 (2003).

Kawai M., et al., "Production of Hydrogen and Hydocarbon From Cellulose and Water," Chemistry Letters 1981 pp. 1185-1188.

Minowa, T., et al., "Hydrogen production from Wet Cellulose by Low Temperature Gasification Using a reduced Nickel Catalyst," Chemistry Letters 1995 pp. 937-938.

Minowa, T., et al., "Hydrogen production from Cellulose in Hot Compressed Water using Reduced Nickel Catalyst: Product Distribution at Different Reaction Temperatures," J. of Chem. Eng. of Japan 31:488-491 (1998).

Miyazawa, T., et al., "Glycerol conversion in the aqueous solution under hydrogen over Ru/C + an ion-exchange resin and its reaction mechanism," J. of Catalysis 240:213-221 (2006).

Nelson, D.A., et al., "Application of Direct Thermal Liquefaction for the Conversion of Cellulosic Biomass," Ind. Eng. Chem. Prod. Res. Dev. 23:471-475 (1984).

Oregon Cellulose-Ethanol Study, Appendix B Overview of Cellulose-Ethanol Production Technology.

Rostrup-Nielsen,J.R., "Conversion of hydrocarbons and alcohols for fuel cells," Phys. Chem. Chem. Phys. 3:283-288 (2001).

Davda, R.R., et al., "Aqueous-phase reforming of ethylene glycol on silica-supported metal catalysts," Applied Catalysis B: Environmental 43:13-26 (2003).

Shabaker, J.W., et al., Aqueous-phase reforming of oxygenated hydrocarbons over Sn-modified Ni catalysts, J. of Catalysis 222:180-191 (2004).

Wang, D., et al., "Catalytic steam reforming of biomass-derived oxygenates: acetic acid and hydroxyacetaldehyde," Applied Catalysis A: General 143:245-270 (1996).

Yoshida, T., et al., "Gasification of Cellulose, Xylan, and Lignin Mixtures in Supercritical Water," Ind. Eng. Chem. Res. 40:5469-5474 (2001).

Gayubo et al., "Transformation of Oxygenate Components of Biomass Pyrolysis Oil on a HZSM-5 Zeolite. I. Alcohols and Phenols," Ind. Eng. Chem Res. 2004, 43:2610-2618.

Gayubo et al., "Transformation of Oxygenate Components of Biomass Pyrolysis Oil on a HZSM-5 Zeolite. Aldehydes, Ketones, and Acids," Ind. Eng. Chem Res. 2004, 43:2619-2626.

US 7,989,664 B2

METHODS AND SYSTEMS FOR GENERATING POLYOLS

RELATED APPLICATIONS

This application is a continuation of U.S. application Ser. No. 11/800,671 filed May 7, 2007, now U.S. Pat. No. 7,767,867, which claimed the benefit of U.S. provisional application 60/798,484 filed May 8, 2006. Each application is incorporated herein by reference in its entirety.

FEDERAL FUNDING STATEMENT

This invention was made with United States government support awarded by DOC NIST Grant No 70NANB3H3014 and DOE Grant No. DE-FG36-05GO15046. The United States has certain rights in this invention.

TECHNICAL FIELD

The present invention is directed to methods, catalysts and reactor systems for generating one or more oxygenated hydrocarbon products from an aqueous feedstock stream containing a water-soluble oxygenated hydrocarbon. Preferably, the reaction products include diols and other polyols, ketones, aldehydes, carboxylic acids and/or alcohols produced by hydrogenating water-soluble polyols (such as glycerol) in a biomass-derived feedstock using hydrogen produced within a reactor system from a portion of the biomass feedstock stream.

BACKGROUND

Biomass (material derived from living or recently living biological materials) is becoming one of the most important renewable energy resources. The ability to convert biomass to fuels, chemicals, energy and other materials is expected to strengthen rural economies, decrease dependence on oil and gas resources, and reduce air and water pollution. The generation of energy and chemicals from renewable resources such as biomass also reduces the net rate of carbon dioxide production, an important greenhouse gas that contributes to global warming.

A key challenge for promoting and sustaining the use of biomass in the industrial sector is the need to develop efficient and environmentally benign technologies for converting biomass to useful products. Present biomass conversion technologies unfortunately tend to carry additional costs which make it difficult to compete with products produced through the use of traditional resources, such as fossil fuels. Such costs often include capital expenditures on equipment and processing systems capable of sustaining extreme temperatures and high pressures, and the necessary operating costs of heating fuels and reaction products, such as fermentation organisms, enzymatic materials, catalysts and other reaction chemicals.

One alternative fuel technology receiving significant attention is biodiesel produced via the esterification of vegetable oils or animal fats. The US production of biodiesel is reaching 30-40 million gallons annually, but is projected to grow to a targeted 400 million gallons of production per year by 2012. In Europe, over 1.4 metric tons of biodiesel was produced in 2003, and major initiatives are underway in Brazil and Asia.

A byproduct of the biodiesel process is crude glycerol, which has little or no value without further refinement. The issue is what to do with the escalating supply of crude glycerol. Purification of crude glycerol is one option, however, the refining of crude glycerol, which contains catalyst, organic impurities and residual methanol, is difficult and often too expensive for small scale biodiesel producers. To complicate matters, the demand for pure glycerol has also remained static and prices have dropped dramatically as more supply is brought on line, especially in Europe.

The development of effective methods to convert crude glycerol to alternative products, such as diols and other polyols, ketones, aldehydes, carboxylic acids and alcohols, may provide additional opportunities to improve the cost effectiveness and environmental benefits of biodiesel production. For example, over a billion pounds of propylene glycol is produced in the United States today and used in the manufacture of many industrial products and consumer products, including aircraft and runway deicing fluids, antifreeze, coolants, heat transfer fluids, solvents, flavors and fragrances, cosmetic additives, pharmaceuticals, hydraulic fluids, chemical intermediates, and in thermoset plastics. Propylene glycol is currently produced via the partial oxidation of fossil fuel derived propylene to form propylene oxide, which is then reacted with water to form propylene glycol.

Researchers have recently developed methods to react pure hydrogen with larger biomass-derived polyols (glycerol, xylitol, and sorbitol) and sugars (xylose and glucose) over hydrogenation and hydrogenolysis catalytic materials to generate propylene glycol. While the biomass is derived from a renewable source, the pure hydrogen itself is generally derived through the steam reforming of non-renewable natural gas. Due to its origin, the pure hydrogen must also be transported to and introduced into the production stream at elevated pressures from an external source, thereby decreasing the efficiency of the process and causing an increase in the overall cost of the ultimate end-product.

For instance, U.S. Pat. Nos. 6,841,085, 6,677,385 and 6,479,713 to Werpy et al., disclose methods for the hydrogenolysis of both carbon-oxygen and carbon-carbon bonds using a rhenium (Re)-containing multimetallic catalyst in the presence of external hydrogen to produce products such as propylene glycol (PG). The Re-containing catalyst may also include Ni, Pd, Ru, Co, Ag, Au, Rh, Pt, Ir, Os and Cu. The conversion takes place at temperatures in a range from 140° C. to 250° C., and more preferably 170° C. to 220° C., and a hydrogen pressure between 600 psi to 1600 psi hydrogen.

Dasari et al. also disclose hydrogenolysis of glycerol to PG in the presence of hydrogen from an external source, at temperatures in a range from 150° C. to 260° C. and a hydrogen pressure of 200 psi, over nickel, palladium, platinum, copper and copper-chromite catalysts. The authors reported increased yields of propylene glycol with decreasing water concentrations, and decreasing PG selectivity at temperatures above 200° C. and hydrogen pressures of 200 psi. The authors further reported that nickel, ruthenium and palladium were not very effective for hydrogenating glycerol. Dasari, M. A.; Kiatsimkul, P.-P.; Sutterlin, W. R.; Suppes, G. J. *Low-pressure hydrogenolysis of glycerol to propylene glycol* Applied Catalysis, A: General, 281(1-2), p. 225 (2005).

U.S. patent application Ser. No. 11/088,603 (Pub. No. US2005/0244312 A1) to Suppes et al., disclose a process for converting glycerin into lower alcohols having boiling pointes less than 200° C., at high yields. The process involves the conversion of natural glycerin to propylene glycol through an acetol intermediate at temperatures from 150° C. to 250° C., at a pressure ranging from 1 to 25 bar (14.5 to 363 psi), and preferably from 5 to 8 bar (72.5 to 116 psi), over a palladium, nickel, rhodium, zinc, copper, or chromium catalyst. The reaction occurs in the presence or absence of hydrogen, with the hydrogen provided by an external source. The glycerin is reacted in solution containing 50% or less by weight water, and preferably only 5% to 15% water by weight.

SUMMARY

The present invention is directed to methods for generating oxygenated hydrocarbons, such as polyols, diols, ketones, aldehydes, carboxylic acids and alcohols, from an aqueous feedstock solution using hydrogen produced from a portion of the feedstock solution. The method involves the reaction of a portion of the feedstock solution over a first catalyst under aqueous phase reforming conditions to produce hydrogen, and reacting the hydrogen with at least a second portion of the feedstock solution over a second catalyst under conditions appropriate to produce the desired products (e.g., by hydrogenation). In one embodiment, the method includes the steps of (a) contacting a first catalytic material with an aqueous feedstock solution containing water and at least one water soluble oxygenated hydrocarbon having two or more carbon atoms to produce hydrogen, and (b) reacting the hydrogen with the remaining oxygenated hydrocarbons over a second catalytic material selected to promote the hydrogenation of the oxygenated hydrocarbons to the desired reactant products.

The aqueous feedstock solution preferably includes water and an oxygenated hydrocarbon having at least two carbon atoms, such as any one of a number of polyols, sugars, sugar alcohols, alcohols, starches, lignins, cellulosics and water soluble saccharides. Preferably, the feedstock solution includes glycerol.

The first catalytic material is desirably a heterogeneous catalyst having one or more materials capable of producing hydrogen under aqueous phase reforming conditions, such as Group VIIIB metals, whether alone or in combination with Group VIIB metals, Group VIB metals, Group VB metals, Group IVB metals, Group JIB metals, Group IB metals, Group IVA metals, or Group VA metals. The second catalytic material is preferably a heterogeneous catalyst having one or more materials capable of catalyzing a reaction between the generated hydrogen and the feedstock solution to produce diols or other polyols, ketones, aldehydes, carboxylic acids and/or alcohols. Preferred examples of the second catalytic material include copper Group VIII metals, mixtures and alloys thereof, and various bifunctional catalysts. The second catalytic material may include these metals alone or in combination with one or more Group VIIIB, VIIB metals, Group VIB metals, Group VB metals, Group IVB metals, Group IIB metals, Group IB metals, Group WA metals, or Group VA metals. Preferably, the second catalytic material includes iron, ruthenium, copper, rhenium, cobalt or nickel.

In one embodiment, polyols, diols, ketones, aldehydes, carboxylic acids and/or alcohols are generated by producing hydrogen from a portion of the aqueous feedstock solution placed in contact with a first catalytic material at a temperature from about 80° C. to 400° C., a weight hourly space velocity (WHSV) of at least about 1.0 gram of oxygenated hydrocarbon per gram of first catalytic material per hour and a pressure where the water and the oxygenated hydrocarbons are condensed liquids, and then reacting the hydrogen with a second portion of the feedstock solution over a second catalytic material under conditions of temperature, pressure and weight hourly space velocity effective to produce one or more oxygenated hydrocarbons, such as diols and other polyols, ketones, aldehydes, carboxylic acids and/or alcohols. The second portion of the feedstock solution will generally include both original oxygenated hydrocarbons and oxygenated hydrocarbons resulting from the hydrogen production step, and may be contacted with the second catalytic material at a temperature from about 100° C. to 300° C., a pressure from about 200 psig to about 1200 psig and a weight hourly space velocity of at least about 1.0 gram of oxygenated hydrocarbon per gram of catalytic material per hour per hour. The resulting composition may generally include, without limitation, a multiphase composition of matter having a solid phase with a catalyst composition containing the first catalytic material and the second catalytic material, preferably platinum and iron, and a fluid phase containing water, glycerol, carboxylic acid, propylene glycol and carbon dioxide.

In another embodiment, reactor systems are provided for producing oxygenated compounds, such as diols or other polyols, ketones, aledhydes, carboxylic acids and/or alcohols, from a polyol. The reactor system includes at least a first reactor bed adapted to receive an aqueous feedstock solution to produce hydrogen and a second reactor bed adapted to produce the oxygenated compounds from the hydrogen and a portion of the feedstock solution. The first reactor bed is configured to contact the aqueous feedstock solution in a condensed phase with a first catalytic material (described above) to provide hydrogen in a reactant stream. The second reactor bed is configured to receive the reactant stream for contact with a second catalytic material (described above) and production of the desired oxygenated compounds. In one preferred embodiment, the first catalytic material includes a Group VIII metal, while the second catalytic material is either iron, ruthenium, copper, rhenium, cobalt, nickel or alloys or mixtures thereof. The second reactor bed may be positioned within the same reactor vessel along with the first reaction bed or in a second reactor vessel in communication with a first reactor vessel having the first reaction bed. The reactor vessel preferably includes an outlet adapted to remove the product stream from the reactor vessel.

DETAILED DESCRIPTION

Figure 1:
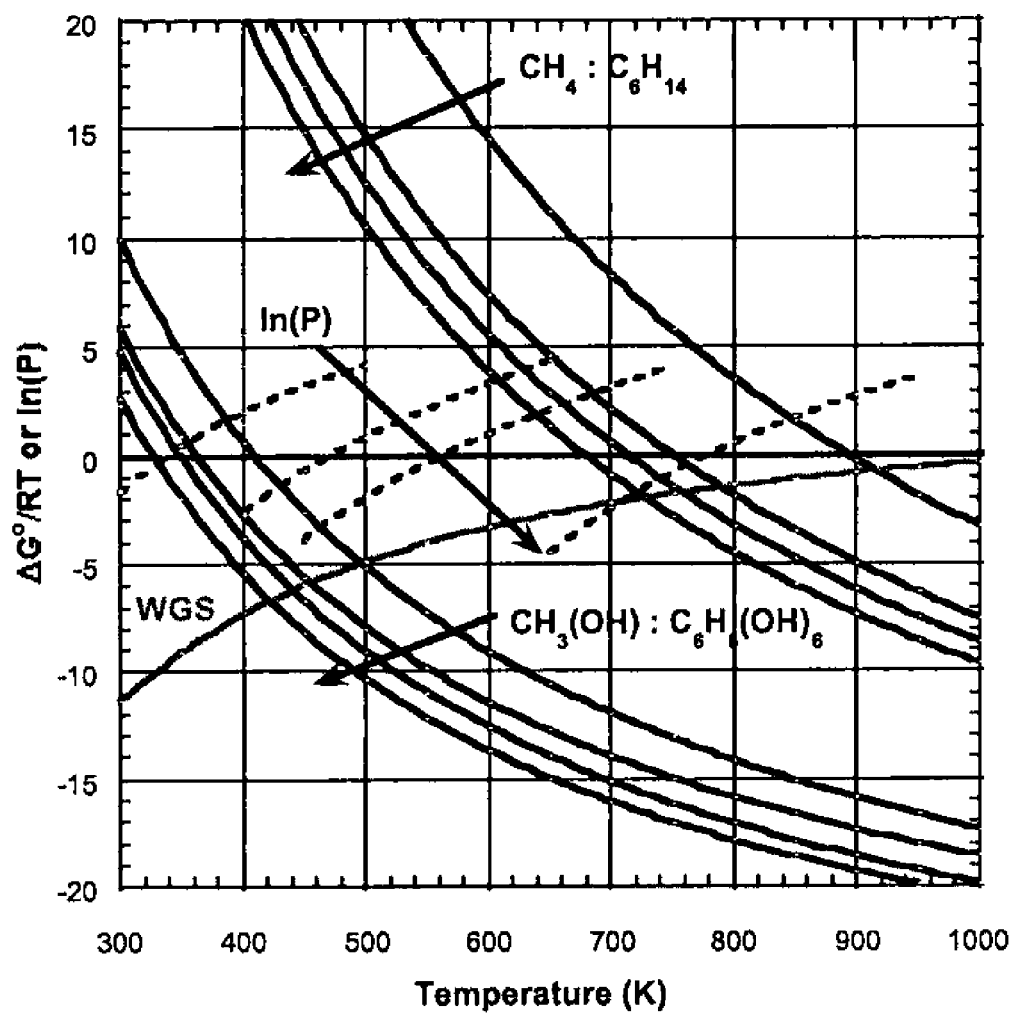
FIG. 1 is a graph depicting the thermodynamics ($\Delta G°/RT$ versus temperature) for the production of CO and $H_2$ from vapor-phase reforming of $CH_4$, $C_2H_6$, $C_3H_8$ and $C_6H_{14}$; $CH_3(OH)$, $C_2H_4(OH)_2$, $C_3H_5(OH)_3$ and $C_6H_8(OH)_6$; and water-gas shift. Dotted lines show values of ln(P) for the vapor pressures versus temperature of $CH_3(OH)$, $C_2H_4(OH)_2$, $C_3H_5(OH)_3$, and $C_6H_8(OH)_6$ (pressure in units of atm).

The present disclosure relates to methods and systems for reforming concentrations of biomass with water at low temperatures to produce propylene glycol, ethylene glycol and other polyols, diols, ketones, aldehydes, carboxylic acids and/or alcohols using in-situ generated hydrogen. The hydrogen may be generated by reacting a portion of an aqueous feedstock solution containing the biomass and water over a catalyst under aqueous phase reforming (APR) conditions. The hydrogen generated by APR may then be used to react with a second portion of the feedstock solution, including the oxygenated hydrocarbons derived from the production of the APR hydrogen, over a second catalyst under conditions appropriate to produce the desired products.

ABBREVIATIONS AND DEFINITIONS

"GC"=gas chromatograph or gas chromatography.
"GHSV"=gas hourly space velocity.
"psig"=pounds per square inch relative to atmospheric pressure (i.e., gauge pressure).
"Space Velocity"=the mass/volume of reactant per unit of catalyst per unit of time.
"TOF"=turnover frequency.
"WHSV"=weight hourly space velocity=mass of oxygenated compound per mass of catalyst per hour.
"WGS"=water-gas shift.

Aqueous-Phase Reforming (APR) is a catalytic reforming process that generates hydrogen-rich fuels from oxygenated compounds derived from biomass (glycerol, sugars, sugar alcohols, etc.). Various APR methods and techniques are described in U.S. Pat. Nos. 6,699,457; 6,964,757 and 6,964,758; and U.S. patent application Ser. No. 11;234,727 (all to Cortright et al., and entitled "Low-Temperature Hydrogen Production from Oxygenated Hydrocarbons"); and U.S. Pat. No. 6,953,873 (to Cortright et al., and entitled "Low Temperature Hydrocarbon Production from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference. The term "aqueous phase reforming" and "APR" shall generically denote the overall reaction of an oxygenated compound and water to yield a hydrogen stream, regardless of whether the reactions takes place in the gaseous phase or in the condensed liquid phase. Where the distinction is important, it shall be so noted. "APR hydrogen" shall generically refer to the hydrogen produced by the APR process.

The APR process is preferably performed in the liquid phase, although it may also be carried out in a vapor phase reaction. APR can occur at temperatures where the water-gas shift reaction is favorable (e.g., 80° C. to 400° C.), making it possible to generate hydrogen with low amounts of CO in a single chemical reactor. Advantages of the APR process include: (i) the performance of the reaction at lower pressures (typically at 200 to 725 psig); (ii) the ability to generate a hydrogen-rich feedstock at lower temperatures without the need to volatilize water, which provides a major energy savings; (iii) the ability to operate at temperatures that minimize undesirable decomposition reactions typically encountered when carbohydrates are heated to elevated temperatures; and (iv) the utilization of agricultural derived feedstocks. The APR process takes advantage of the unique thermodynamic properties of oxygenated compounds having a favorable carbon-to-oxygen stoichiometry, especially hydrocarbons having a C:O ratio of 1:1 (the preferred ratio), to generate hydrogen at relatively low temperatures in a single reaction step.

The stoichiometric reaction for reforming an oxygenated hydrocarbon having a C:O ratio of 1:1 to produce CO and $H_2$ is given by reaction 1.

$$C_nH_{2y}O_n \leftrightarrow nCO + yH_2 \quad (1)$$

Reaction conditions for producing hydrogen from hydrocarbons can be dictated by the thermodynamics for the steam reforming of alkanes to form CO and $H_2$ (reaction 2), and the water-gas shift reaction to form $CO_2$ and $H_2$ from CO (reaction 3).

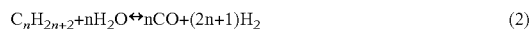
$$C_nH_{2n+2} + nH_2O \leftrightarrow nCO + (2n+1)H_2 \quad (2)$$

$$CO + H_2O \leftrightarrow CO_2 + H_2 \quad (3)$$

FIG. 1 (constructed from thermodynamic data obtained from Chemical Properties Handbook, C. L. Yaws, McGraw Hill, 1999) shows changes in the standard Gibbs free energy ($\Delta G°/RT$) associated with equation 2 for a series of alkanes ($CH_4$, $C_2H_6$, $C_3H_8$, $C_6H_{14}$), normalized per mole of CO produced. It can be seen that the steam reforming of alkanes is thermodynamically favorable (i.e., negative values of $\Delta G°/RT$) only at temperatures higher than 675 K (402° C.).

Relevant oxygenated hydrocarbons having a C:O ratio of 1:1, such as methanol ($CH_3OH$), ethylene glycol ($C_2H_4(OH)_2$), glycerol ($C_3H_5(OH)_3$), and sorbitol ($C_6H_8(OH)_6$), are also illustrated. On FIG. 1, dotted lines show values of ln(P) for the vapor pressures versus temperature of $CH_3(OH)$, $C_2H_4(OH)_2$, $C_3H_5(OH)_3$, and $C_6H_8(OH)_6$ (pressure in units of atm). FIG. 1 shows that steam reforming of these oxygenated hydrocarbons to produce CO and $H_2$ is thermodynamically favorable at significantly lower temperatures than those required for alkanes with similar numbers of carbon atoms. FIG. 1 also shows that the value of $\Delta G°/RT$ for water-gas shift of CO to $CO_2$ and $H_2$ is more favorable at similarly low temperatures. Consequently, it is possible to reform oxygenated hydrocarbons with favorable C:O ratios at low-temperatures to form CO and $H_2$, and subsequently $H_2$ and $CO_2$, in a single-step catalytic process.

While FIG. 1 shows that the conversion of oxygenated compounds in the presence of water to $H_2$ and $CO_2$ is highly favorable at low temperatures, the subsequent reaction of $H_2$ and oxygenated compounds to form alkanes ($C_nH_{2n+2}$) and water is also highly favorable at low temperatures.

$$CO_2 + 4H_2 \leftrightarrow CH_4 + 2H_2O \quad (4)$$

In a first embodiment, methods for generating oxygenated compounds are provided. The methods preferably include the steps of (a) contacting a first catalytic material with a first portion of an aqueous feedstock solution containing water and water soluble oxygenated hydrocarbons to form APR hydrogen, and (b) contacting the APR hydrogen and a second portion of the feedstock solution over a second catalytic material to produce a reaction product that includes, without limitation, a polyol, diol, ketone, aldehyde, carboxylic acid and/or alcohol. The second portion of the feedstock solution preferably includes oxygenated hydrocarbons derived from the production of the APR hydrogen in addition to oxygenated hydrocarbons included in the original feedstock solution, but may also include portions of the feedstock solution without oxygenated hydrocarbons generated during APR hydrogen formation. The first catalytic material is preferably an aqueous phase reforming (APR) catalyst, and the second catalytic material is preferably a material capable of catalyzing hydrogenation reactions. Unless otherwise indicated, any discussion of hydrogenation catalysts and APR catalysts herein are non-limiting examples of suitable catalytic materials.

As described more fully below, the more thermodynamically favored reaction consumes APR hydrogen to yield a mixture of polyols, diols, ketones, aldehydes and/or alcohols. Under favorable conditions, the processes and reactor systems described below may yield a mixture predominantly comprising one or more oxygenated compounds, such as diols and other polyols, ketones, aldehydes, carboxylic acids and/or alcohols. For example, processes and reactor systems described herein may provide a carbon containing reaction product with more than 50% of one or more polyols, such as propylene glycol. Preferably, substantially all of the APR hydrogen generated in-situ by the APR process is consumed during the reaction with the oxygenated hydrocarbons over the second catalytic material, without the addition of pure hydrogen from an external source.

Figure 2:
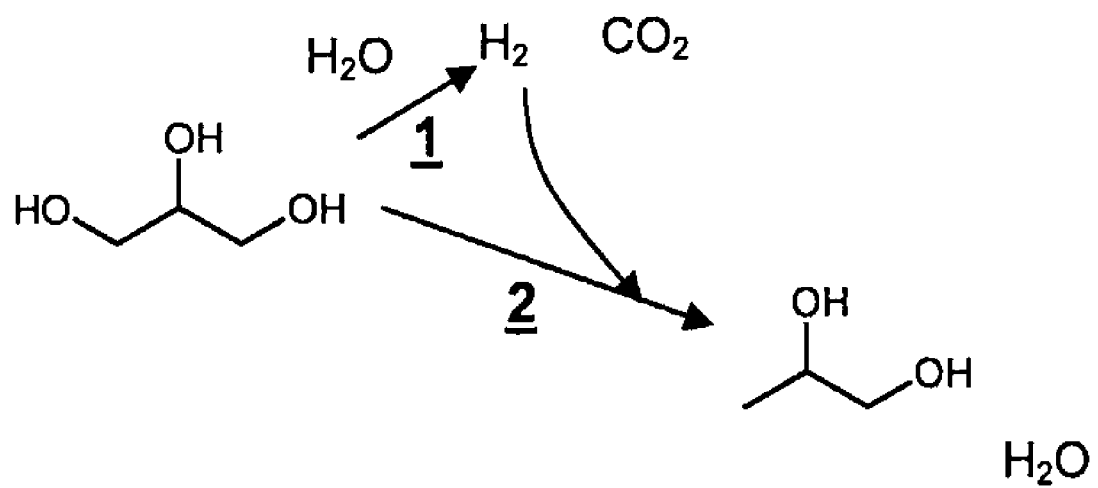
FIG. 2 is a reaction schematic depicting reaction pathways for the production of $H_2$ and propylene glycol from glycerol.
Figure 3:
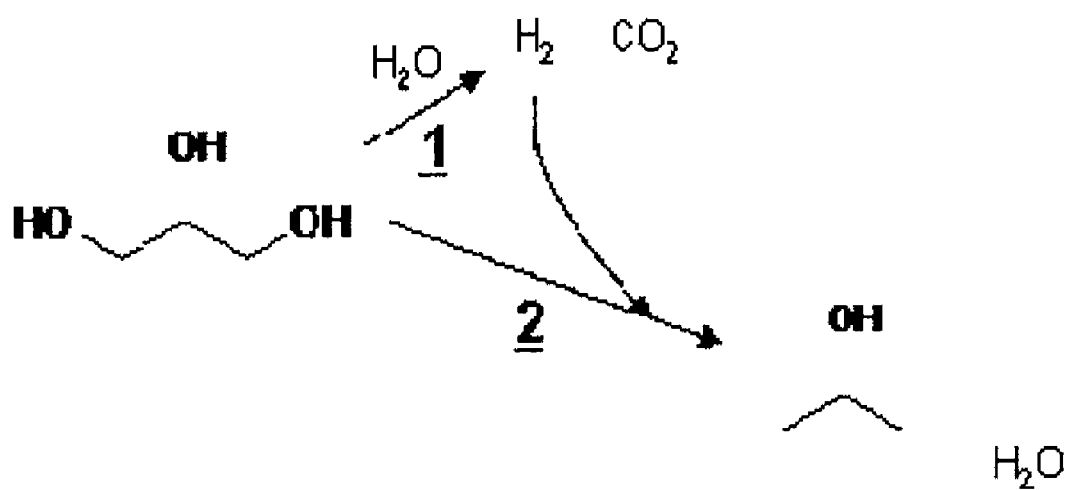
FIG. 3 is a reaction schematic depicting reaction pathways for the production of $H_2$ and propyl alcohol from glycerol.
Figure 4:
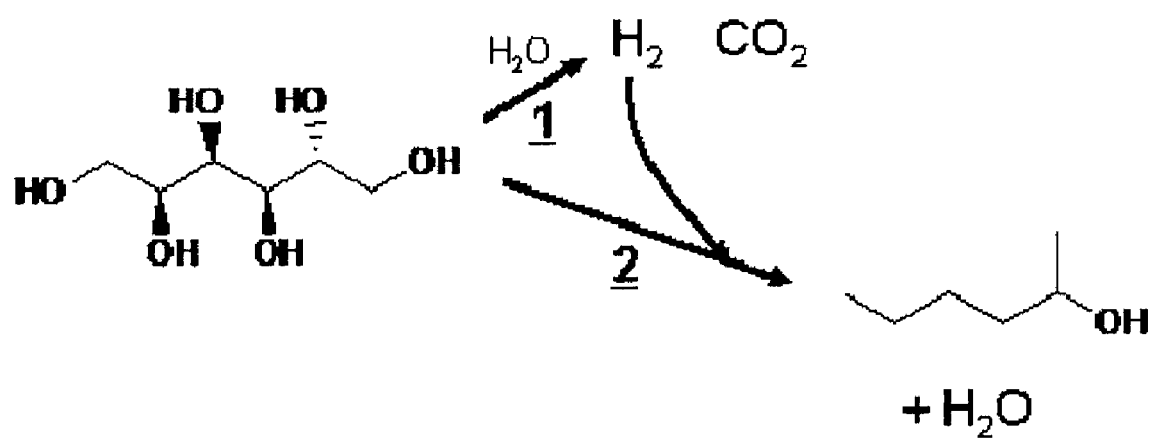
FIG. 4 is a reaction schematic depicting reaction pathways for the production of $H_2$ and hexanol from sorbitol.

FIGS. 2, 3 and 4 show schematic representations of possible reaction pathways for the formation of both $H_2$ and polyols, diols, ketones and alcohols from oxygenated hydrocarbons over a metal catalyst. In general, hydrogen formation involves dehydrogenation and subsequent rearrangement steps that form intermediates containing carbon atoms unbound to oxygen atoms. The carbohydrate first undergoes dehydrogenation to provide adsorbed intermediates, prior to cleavage of C—C or C—O bonds. Subsequent cleavage of C—C bonds leads to the formation of CO and $H_2$, with the CO then reacting with water to form $CO_2$ and $H_2$ by the water-gas shift (WGS) reaction. The formation of polyols, diols, ketones, carboxylic acids, aldehydes, and/or alcohols follows where the hydroxyl groups of the oxygenated hydrocarbon are removed via a dehydration mechanism with subsequent hydrogenation with the hydrogen formed above. It's also possible to form polyols, diols, ketones and/or alcohols on the metal catalyst by first cleaving C—O bonds in adsorbed carbohydrate intermediates. The intermediates can then be converted to the polyol, diol, ketone, carboxylic acid, aldehyde, and/or alcohol depending on the catalyst and reaction conditions.

Feedstock Solution

The preferred feedstock includes water-soluble oxygenated hydrocarbons derived from biomass. As used herein, the term "biomass" refers to, without limitation, organic materials produced by plants (such as leaves, roots, seeds and stalks), and microbial and animal metabolic wastes. Common sources of biomass include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, switch grass, alfalfa, prairie bluestream, corn, soybean, and the like. The feedstock may be fabricated from biomass by any means now known or developed in the future, or may be simply byproducts of other processes, such as crude glycerol from biodiesel production.

The oxygenated hydrocarbons may be any hydrocarbon having at least two carbon atoms and at least one oxygen atom. In the preferred embodiment, the oxygenated hydrocarbon is water-soluble and has from 2 to 12 carbon atoms, and more preferably from 2 to 6 carbon atoms. The oxygenated hydrocarbon also preferably has an oxygen-to-carbon ratio ranging from 0.5:1 to 1.5:1, including ratios of 0.75:1.0, 1.0:1.0, 1.25:1.0, 1.5:1.0 and other ratios there between. In the most preferred embodiment, the oxygenated hydrocarbons have an oxygen-to-carbon ratio of 1:1. Nonlimiting examples of preferred water-soluble oxygenated hydrocarbons include ethanediol, ethanedione, acetic acid, propanol, propanediol, propionic acid, glycerol, glyceraldehyde, dihydroxyacetone, lactic acid, pyruvic acid, malonic acid, butanediols, butanoic acid, aldotetroses, tautaric acid, aldopentoses, aldohexoses, ketotetroses, ketopentoses, ketohexoses, alditols, sugars, sugar alcohols, cellulosics, lignocellulosics, saccharides, starches, polyols and the like. Most preferably, the oxygenated hydrocarbon is sugar, sugar alcohols, cellulose, saccharides and glycerol.

The oxygenated hydrocarbon is combined with water to provide an aqueous feedstock solution having a concentration effective for causing the formation of the desired reaction products. The water may be added either prior to contacting the oxygenated hydrocarbon to the APR catalyst or at the same time as contacting the oxygenated hydrocarbon to the APR catalyst. In the preferred embodiment, the water is combined with the oxygenated hydrocarbon to form an aqueous solution prior to contacting the APR catalyst for easier processing, but it is also recognized that the oxygenated hydrocarbon may also be placed into solution and then supplemented with water at the time of contact with the APR catalyst to form the aqueous feedstock solution. Preferably the balance of the feedstock solution is water. In some embodiments, the feedstock solution consists essentially of water, one or more oxygenated hydrocarbons and, optionally, one or more feedstock modifiers described herein, such as alkali or hydroxides of alkali or alkali earth salts or acids. The feedstock solution may also contain negligible amounts of hydrogen, preferably less than about 1 bar (14.5 psi). In the preferred embodiments, hydrogen is not added to the feedstock.

The water-to-carbon ratio in the solution is preferably from about 0.5:1 to about 7:1, including ratios there between such as 1:1, 2:1, 3:1, 4:1, 5:1, 6:1, and any ratios there between. The feedstock solution may also be characterized as a solution having at least 20 weight percent of the total solution as an oxygenated hydrocarbon. For example, the solution may include one or more oxygenated hydrocarbons, with the total concentration of the oxygenated hydrocarbons in the solution being at least about 20%, 30%, 40%, 50%, 60% or greater by weight, including any percentages between, and depending on the oxygenated hydrocarbons used. More preferably the feedstock solution includes at least about 20%, 30%, 40%, 50%, or 60% of glycerol by weight, including any percentages between. Water-to-carbon ratios and percentages outside of the above stated ranges are also included within the scope of this invention.

Hydrogen Production

The APR hydrogen is produced from the feedstock under aqueous phase reforming conditions. The reaction temperature and pressure are preferably selected to maintain the feedstock in the liquid phase. However, it is recognized that temperature and pressure conditions may also be selected to more favorably produce hydrogen in the vapor-phase. In general, the APR reaction and subsequent hydrogenation reactions should be carried out at a temperature at which the thermodynamics of the proposed reaction are favorable. The pressure will vary with the temperature. For condensed phase liquid reactions, the pressure within the reactor must be sufficient to maintain the reactants in the condensed liquid phase at the reactor inlet.

For vapor phase reactions, the reaction should be carried out at a temperature where the vapor pressure of the oxygenated hydrocarbon compound is at least about 0.1 atm (and preferably a good deal higher), and the thermodynamics of the reaction are favorable. This temperature will vary depending upon the specific oxygenated hydrocarbon compound used, but is generally in the range of from about 100° C. to about 450° C. for reactions taking place in the vapor phase, and more preferably from about 100° C. to about 300° C. for vapor phase reactions.

For liquid phase reactions, the reaction temperature may be from about 80° C. to about 400° C., and the reaction pressure from about 72 psig to about 1300 psig. Preferably, the reaction temperature is between about 120° C. and about 300° C., and more preferably between about 150° C. and about 270° C. The reaction pressure is preferably between about 72 and 1200 psig, or between about 145 and 1200 psig, or between about 200 and 725 psig, or between about 365 and 600 psig. Because the hydrogen is produced in-situ, the pressure is provided by a pumping mechanism that also drives the feedstock solution through the reactor system.

The condensed liquid phase method may also optionally be performed using a modifier that increases the activity and/or stability of the first and/or the second catalytic material(s) (i.e., the catalyst system). It is preferred that the water and the oxygenated hydrocarbon are reacted at a suitable pH of from about 1.0 to about 10.0, including pH values in increments of 0.1 and 0.05 between, and more preferably at a pH of from about 4.0 to about 10.0. Generally, the modifier is added to the feedstock solution in an amount ranging from about 0.1% to about 10% by weight as compared to the total weight of the catalyst system used, although amounts outside this range are included within the present invention.

Alkali or alkali earth salts may also be added to the feedstock solution to optimize the proportion of hydrogen in the reaction products. Examples of suitable water-soluble salts include one or more selected from the group consisting of an alkali or an alkali earth metal hydroxide, carbonate, nitrate, or chloride salt. For example, adding alkali (basic) salts to provide a pH of about pH 4.0 to about pH 10.0 can improve hydrogen selectivity of reforming reactions.

The addition of acidic compounds may also provide increased selectivity to the desired reaction products in the hydrogenation reactions described below. It is preferred that the water-soluble acid is selected from the group consisting of nitrate, phosphate, sulfate, and chloride salts, and mixtures thereof. If an optional acidic modifier is used, it is preferred that it be present in an amount sufficient to lower the pH of the aqueous feed stream to a value between about pH 1.0 and about pH 4.0. Lowering the pH of a feed stream in this manner may increase the proportion of diols, polyols, ketones, carboxylic acids, aldehydes, alcohols or alkanes in the final reaction products.

In general, the reaction should be conducted under conditions where the residence time of the feedstock solution over the APR catalyst is appropriate to generate an amount of APR hydrogen sufficient to react with a second portion of the feedstock solution over the hydrogenation catalyst to provide the desired products. For example, in one embodiment, the WHSV for the reaction may be at least about 1.0 gram of oxygenated hydrocarbon per gram of APR catalyst, and preferably between about 1.0 to 5.0 grams of oxygenated hydrocarbon per gram of APR catalyst, and more preferably between about 1.9 to 4.0 grams of oxygenated hydrocarbon per gram of APR catalyst.

APR Catalyst

The first catalytic material is preferably an APR catalyst, typically a heterogeneous catalyst capable of catalyzing the reaction of water and oxygenated hydrocarbons to form hydrogen under the conditions described above. The preferred APR catalyst includes at least one Group VIIIB transition metal, and any alloy or mixtures thereof. Preferably, the APR catalyst includes at least one Group VIIIB transition metal in combination with at least one second metal selected from Group VIIIB, Group VIIB, Group VIB, Group VB, Group IVB, Group IIB, Group IB, Group IVA or Group VA metals. The preferred Group VIIB metal includes rhenium, manganese, or combinations thereof. The preferred Group VIB metal includes chromium, molybedum, tungsten, or a combination thereof. The preferred Group VIIIB metals include platinum, rhodium, ruthenium, palladium, nickel, or combinations thereof.

Preferred loading of the primary Group VIIIB metal is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second metal is in the range of 0.25-to-1 to 10-to-1, including ratios there between, such as 0.50, 1.00, 2.50, 5.00, and 7.50-to-1.

A preferred catalyst composition is further achieved by the addition of oxides of Group IIIB, and associated rare earth oxides. In such event, the preferred components would be oxides of either lanthanium or cerium. The preferred atomic ratio of the Group IIIB compounds to the primary Group VIIIB metal is in the range of 0.25-to-1 to 10-to-1, including ratios there between, such as 0.50, 1.00, 2.50, 5.00, and 7.50-to-1.

Unless otherwise specified, the recitation of an APR bimetallic catalyst composition as "X:Y" herein, where X and Y are metals, refers to a group of catalyst compositions comprising at least metals X and Y in any suitable stoichoimetric combination, and optionally including other materials. Similarly, the recitation of a catalyst composition as "X1.0Y1.0" refers herein to a composition comprising at least metals X and Y in a 1:1 stoichiometric molar ratio. Accordingly, particularly preferred catalytic compositions are bimetallic metal compositions described by the formula X:Y, where X is a Group VIIIB metal and Y is a Group VIIIB, Group VIIB, Group VIB, Group VB, Group IVB, Group IIB, Group IB, Group WA or Group VA metal. For example, the catalysts designated "Re:Pt" include the bimetallic catalysts $Re_{1.0}Pt_{1.0}$ and $Re_{2.5}Pt_{1.0}$. Furthermore, recitation of a bimetallic catalyst X:Y can include additional materials besides X and Y, such as La or Ce. For example, the catalysts designated "Re:Rh" herein include catalysts such as $Re_{1.0}Rh_{1.0}$, $Re_{1.0}Rh_{3.8}$, $Re_{1.0}Rh_{2.0}Ce_{2.0}$, $Re_{1.0}Rh_{1.0}Ce_{1.0}$, and $Re_{1.0}Rh_{1.0}La_{3.0}$.

In preferred embodiments, the catalyst system may include a support suitable for suspending the catalyst in the feedstock solution. The support should be one that provides a stable platform for the chosen catalyst and the reaction conditions. The support may take any form which is stable at the chosen reaction conditions to function at the desired levels, and specifically stable in aqueous feedstock solutions. Such supports include, without limitation, carbon, silica, silica-alumina, alumina, zirconia, titania, ceria, vanadia and mixtures thereof. Furthermore, nanoporous supports such as zeolites, carbon nanotubes, or carbon fullerene may be utilized. Particularly useful catalyst systems include, without limitation, platinum supported on silica, platinum supported on silica-alumina, platinum supported on alumina, nickel supported on silica-alumina, nickel supported on alumina, ruthenium supported on silica-alumina, ruthenium supported on alumina, palladium supported on silica-alumina, and nickel-platinum supported on silica-alumina. In one embodiment, the APR catalyst system is platinum on silica-alumina or silica, with the platinum being further alloyed or admixed with nickel, ruthenium, copper, iron or rhenium. In another embodiment, the APR catalyst system is nick on silica-alumina or silica, with the nickel being further alloyed or admixed with copper, rhenium, ruthenium or iron.

One particularly preferred catalyst support is carbon, especially carbon supports having relatively high surface areas (greater than 100 square meters per gram). Such carbons include activated carbon (granulated, powdered, or pelletized), activated carbon cloth, felts, or fibers, carbon nanotubes or nanohorns, carbon fullerene, high surface area carbon honeycombs, carbon foams (reticulated carbon foams), and carbon blocks. The carbon may be produced via either chemical or steam activation of peat, wood, lignite, coal, coconut shells, olive pits, and oil based carbon. Another preferred support is granulated activated carbon produced from coconuts.

The support may also be treated or modified to enhance its properties. For example, the support may be treated, as by surface-modification, to modify surface moieties, such as hydrogen and hydroxyl. Surface hydrogen and hydroxyl groups can cause local pH variations that affect catalytic efficiency. The support may also be modified, for example, by treating it with sulfates, phosphates, tungstenates, and silanes. For carbon supports, the carbon may be pretreated with steam, oxygen (from air), inorganic acids or hydrogen peroxide to provide more surface oxygen sites. The preferred pretreatment would be to use either oxygen or hydrogen peroxide. The pretreated carbon may also be modified by the addition of oxides of Group IVB and Group VB. It is preferred to use oxides of titanium, vanadium, zirconia and mixtures thereof.

The APR catalyst system may be prepared using conventional methods known to those in the art. These methods include evaporative impregnation techniques, incipient wetting techniques, chemical vapor deposition, wash-coating, magnetron sputtering techniques, and the like. The method chosen to fabricate the catalyst is not particularly critical to the function of the invention, with the proviso that different catalysts will yield different results, depending upon considerations such as overall surface area, porosity, etc.

Oxygenated Compound Production

Various oxygenated compounds may be produced by the preferred methods and reactor systems. For example, the reaction products may include one or more diols or other polyols, ketones, aldehydes, carboxylic acids and alcohols derived from the reaction of the in-situ generated APR hydrogen with a portion of the remaining feedstock solution over a second catalytic material, preferably a hydrogenation catalyst, under conditions of reaction temperature, reaction pressure and weight hourly space velocity (WHSV) effective to produce the desired reaction products. The temperature and pressure are preferably selected to conduct the reaction in the liquid phase. It is recognized, however, that temperature and pressure conditions may also be selected to more favorably produce the desired products in the vapor-phase. In general, the reaction should be conducted at a temperature where the thermodynamics of the proposed reaction are favorable. The pressure will vary with the temperature and WHSV. For condensed phase liquid reactions, the pressure within the reactor must be sufficient to maintain the reactants in the condensed liquid phase at the reactor inlet.

For liquid phase reactions, the reaction temperature may be from about 100° C. to about 300° C., and the reaction pressure from about 72 psig to about 1300 psig. Preferably, the reaction temperature is between about 120° C. and about 270° C., and more preferably between about 200° C. and about 270° C. The reaction pressure is preferably between about 72 and 1200 psig, or between about 145 and 1200 psig, or between about 200 and 725 psig, or between about 365 and 600 psig.

For vapor phase reactions, the reaction should be carried out at a temperature where the vapor pressure of the oxygenated hydrocarbon compound is at least about 0.1 atm (and preferably a good deal higher), and the thermodynamics of the reaction are favorable. This temperature will vary depending upon the specific oxygenated hydrocarbon compound used, but is generally in the range of from about 100° C. to about 300° C. for vapor phase reactions.

The condensed liquid phase method of the present invention may also be performed using a modifier that increases the activity and/or stability of the catalyst system. It is preferred that the water and the oxygenated hydrocarbon are reacted at a suitable pH of from about 1.0 to about 10.0, including pH values in increments of 0.1 and 0.05 between, and more preferably at a pH of from about 4.0 to about 10.0. Generally, the modifier is added to the feedstock solution in an amount ranging from about 0.1% to about 10% by weight as compared to the total weight of the catalyst system used, although amounts outside this range are included within the present invention.

In general, the reaction should be conducted under conditions where the residence time of the feedstock solution over the catalyst is appropriate to generate the desired products. For example, the WHSV for the reaction may be at least about 1.0 gram of oxygenated hydrocarbon per gram of catalyst per hour, and preferably between about 1.0 to 5.0 grams of oxygenated hydrocarbon per gram of catalyst per hour, and more preferably between about 1.9 to 4.0 grams of oxygenated hydrocarbon per gram of catalyst per hour.

Hydrogenation Catalyst

The second catalytic material is preferably a heterogeneous hydrogenation catalyst capable of catalyzing the reaction of hydrogen and oxygenated hydrocarbons to produce the desired reaction products. The preferred hydrogenation catalyst may include copper or at least one Group VIIIB transition metal, and any alloys or mixtures thereof. The catalyst may also be constructed to include either copper or at least one Group VIIIB transition metal as a first metal, and at least one second metal from the selection of Group VIIIB, Group VIIB, Group VIB, Group VB, Group IVB, Group IIB, Group IB, Group WA or Group VA metals. The preferred Group VIIB metal includes rhenium, manganese, or combinations thereof. The preferred Group VIB metal includes chromium, molybedum, tungsten, or a combination thereof. The preferred Group VIIIB metals include platinum, rhodium, ruthenium, palladium, nickel, or combinations thereof. In one embodiment, the preferred catalyst includes iron or rhenium and at least one transition metal selected from iridium, nickel, palladium, platinum, rhodium and ruthenium. In another embodiment, the catalyst includes iron, rhenium and at least copper or one Group VIIIB transition metal.

The second catalytic material is preferably a hydrogenation catalyst that is different from the first catalytic material, which is preferably an APR catalyst, or a second catalyst capable of working in parallel with or independently of the APR catalyst. The hydrogenation catalyst may also be a bi-functional catalyst. For example, acidic supports (e.g., supports having low isoelectric points) are able to catalyze dehydration reactions of oxygenated compounds, followed by hydrogenation reactions on metallic catalyst sites in the presence of $H_2$, again leading to carbon atoms that are not bonded to oxygen atoms. The bi-functional dehydration/hydrogenation pathway consumes $H_2$ and leads to the subsequent formation of various polyols, diols, ketones, aldehydes and alcohols. Examples of such catalysts include tungstated zirconia, titania zirconia, sulfated zirconia, acidic alumina, silica-alumina, and heteropolyacid supports. Heteropolyacids are a class of solid-phase acids exemplified by such species as $H_{3+x}PMo_{12-x}V_xO_{40}$, $H_4SiW_{12}O_{40}$, $H_3PW_{12}O_{40}$, $H_6P2W_{18}O_{62}$, and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net (−3) charge, and thus requires 3 cations to satisfy electroneutrality. If the cationic are protons, the material functions as a Bronsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Micro-calorimetry and Density Functional Quantum Chemical Calculations," *J. or Physical Chemistry B*, 102:10817-10825.

Similar to the APR catalyst, the hydrogenation catalyst may be adhered to a support as described above. The support may be the same support as used for the APR catalyst or a support specific to the hydrogenation catalyst as selected for the desired reaction outcome.

Preferred loading of the copper or primary Group VIIIB metal is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second metal is in the range of 0.25-to-1 to 10-to-1, including any ratios between such as 0.50, 1.00, 2.50, 5.00, and 7.50-to-1. In one embodiment, the hydrogenation catalyst includes iron (Fe), a Group VIIIB metal, with an atomic ratio of Fe to the primary Group VIIIB metal from 0.25-to-1 to 10-to-1. If the catalyst is adhered to a support, the combination of the catalyst and the support is from 0.25 wt % to 10 wt % of the copper or primary Group VIIIB metal.

The heterogeneous catalyst may also be combined with the APR catalyst to form a mixture so as to allow the APR reaction and the hydrogenation reaction to occur simultaneously, or nearly simultaneously, in a single reactor vessel. In such event, the recitation of a bimetallic catalyst composition as "X:Y", where X is an APR catalyst and Y is a hydrogenation catalyst, shall refer to a group of catalyst compositions comprising at least APR catalyst X and hydrogenation catalyst Y, in any suitable stoichoimetric combination and including other materials when indicated. For example, the catalysts designated "Pt:Fe" includes the mixture $Pt_{1.0}Fe_{1.0}$ and $Pt_{2.5}Fe_{1.0}$. Particularly preferred catalysts include $Pt_{1.0}Ni_{1.0}Fe_{1.0}$ and $Pt_{1.0}Fe_{1.0}Cu_{1.0}$, where Pt and Pt:Ni represent the APR catalyst and Fe and Fe:Cu represent the hydrogenation catalyst.

The preferred atomic ratio of the APR catalyst (first catalytic material) to the hydrogenation catalyst (second catalytic material) is in the range of 5:1 to 1:5, such as, without limitation, 4.5:1, 4.0:1, 3.5:1, 3.0:1, 2.5:1, 2.0:1, 1.5:1, 1:1, 1:1.5, 1:2.0, 1:2.5, 1:3.0, 1:3.5, 1:4.0, 1:4.5, and any amounts there between. For example, in one embodiment, a catalyst mixture is provided the APR catalyst including platinum and the hydrogenation catalyst including iron (Pt:Fe) at a ratio of 1:1. If the catalyst mixture is adhered to a support, the combination of the catalyst and the support may be from 0.25 wt % to 10 wt % of the mixture.

The hydrogenation catalyst system, whether alone or mixed with the APR catalyst, may be prepared using conventional methods known to those in the art. Such methods include evaporative impregnation, incipient wetting, chemical vapor deposition, wash-coating, magnetron sputtering techniques, and the like. The method chosen to fabricate the catalyst is not particularly critical to the function of the invention, with the proviso that different catalysts will yield different results, depending upon considerations such as overall surface area, porosity, etc.

Reactor

The reaction system can be configured such that the flow direction of the aqueous feedstock solution can be selected to ensure maximal interaction of the in-situ generated hydrogen with the feedstock solution. For example, the reactor may be designed so that an APR catalyst and a hydrogenation catalyst are stacked in a single reaction vessel, or separated so that the APR catalyst and hydrogenation catalyst are in separate reaction vessels. The reactor may also be designed to accommodate multiple APR catalysts and hydrogenation catalysts so as to allow for optimal production of more than one reaction product. The reactor system may also include additional inlets to allow for the introduction of supplemental materials to further advance or direct the reaction to the desired reaction products, and to allow for the recycling of reaction byproducts for use in the reforming process.

The reactor may be designed so that the feedstock solution flows horizontally, vertical or diagonally to the gravitational plane so as to maximize the efficiency of the system. In systems where the feedstock solution flows vertically or diagonally to the gravitational plan, the feedstock solution may flow either against gravity (up-flow system) or with gravity (down-flow system). In one preferred embodiment, the reactor is designed as an up-flow system such that the feedstock solution flows through the reactor in an upwards direction. In this embodiment, the feedstock solution first contacts a first reaction bed containing the APR catalyst to produce APR hydrogen. Due to the configuration of the reactor, the APR hydrogen is then able to, under certain conditions, percolate through a second reaction bed containing the hydrogenation catalyst at a rate greater than or equal to the feedstock solution to maximize the interaction of the feedstock solution with the hydrogen and hydrogenation catalyst.

In a reactor with a single chamber, the APR catalyst and hydrogenation catalyst may be placed in a stacked configuration to allow the feedstock solution to first contact the APR catalyst and then the hydrogenation catalyst, or a series of hydrogenation catalysts depending on the desired reaction products. The reaction beds for the APR catalyst and hydrogenation catalyst, or catalysts, may also be placed side-by-side dependent upon the particular flow mechanism employed, such as a horizontal flow system. In either case, the feedstock solution may be introduced into the reaction vessel through one or more inlets, and then directed across the catalysts for processing. In the preferred embodiment, the feedstock solution is directed across the APR catalyst to produce APR hydrogen, and then both the APR hydrogen and the remaining feedstock solution are directed across the hydrogenation catalyst, or catalysts, to produce the desired reaction products. In embodiments employing a mixture of APR catalyst and hydrogenation catalyst, the generation of the APR hydrogen and the reaction products may occur simultaneously or in parallel.

In a separate reactor configuration, the reactor may be designed to allow for APR hydrogen production to occur in a reaction bed in one reaction vessel with the reaction products generated in another reaction vessel. The reaction vessels may be configured to run in parallel or sequentially. In a parallel configuration, the feedstock solution may be separated to direct a first portion of the feedstock solution to the hydrogen reaction bed where APR hydrogen is produced, and a second portion to a hydrogenation reaction bed where the desired reaction products are produced using APR hydrogen generated by the hydrogen reaction vessel. Alternatively, the reactor may be configured to accommodate the use of two separate feedstock solutions, with the first feedstock solution directed to the hydrogen reaction vessel and the second feedstock solution directed to the hydrogenation reaction vessel. In a sequential configuration, the reactor may be designed so that the feedstock solution flows through the hydrogen reaction vessel and into the hydrogenation reaction vessel. In either of these systems, because the APR hydrogen is produced in-situ, the pressure is provided by a pumping mechanism that also drives the feedstock solution through the reactor chambers.

Supplemental Materials

Supplemental materials and compositions ("supplements") may be added to the feedstock solution at various stages of the process in order to enhance the reaction or to drive it to the production of the desired reaction products. Supplements may include, without limitation, acids, salts and additional hydrogen or feedstock. Such supplements may be added directly to the feedstock stream prior to or contiguous with contacting the hydrogenation catalyst, or directly to the reaction bed for the hydrogenation reaction.

In one embodiment, the supplement may include an additional feedstock solution for providing additional oxygenated hydrocarbons for the hydrogenation reaction. The feedstock may include any one or more oxygenated hydrocarbons listed above, including any one or more sugar alcohols, glucose, polyols, glycerol or saccharides. For instance, the supplemental material may include glycerol. In this embodiment, crude glycerol is used to initiate the reaction and to produce hydrogen so as to avoid polluting the hydrogenation catalyst with contaminants from the crude glycerol. Purified glycerol is then added to the feedstock solution prior to or at the same time the original feedstock solution is placed in contact with the hydrogenation catalyst to increase the oxygenated hydrocarbons available for processing. It is anticipated that the opposite may be employed with the crude glycerol serving as the supplement depending on the characteristics of the APR catalyst and hydrogenation catalyst.

In another embodiment, the supplement may include byproducts of the present invention recycled for further processing. The byproducts may include diols, polyols, ketones, aldehydes, carboxylic acids, alcohols and other products generated by the practice of the present invention. For example, the desired reaction product of one embodiment of the present invention is propylene glycol. However, the production of propylene glycol may also result in the production of other polyols, ketones, aldehydes, alcohols and carboxylic acids. The polyols may be recycled and added back into the feedstock solution prior to contact with the hydrogenation catalysts in order to provide supplemental oxygenated hydrocarbons for conversion to propylene glycol. Similarily, ketones and alcohols may be added to the feedstock solution prior to contact with the APR catalyst to further supplement the production of hydrogen.

In yet another embodiment, the supplemental material may include acids and salts. The addition of acidic compounds may provide increased selectivity to the desired reaction products. In the preferred embodiments, the water-soluble acid may include, without limitation, nitrate, phosphate, sulfate, chloride salts, and mixtures thereof. If an optional acidic modifier is used, it is preferred that it be present in an amount sufficient to lower the pH of the aqueous feed stream to a value between about pH 1.0 and about pH 4.0. Lowering the pH of a feed stream in this manner may increase the proportion of diols, polyols, ketones, alcohols or alkanes in the final reaction products.

In another embodiment, the supplement may include additional hydrogen added to the feedstock solution to supplement the APR hydrogen and to help drive the hydrogenation reaction to a desired reaction product. The term "supplemental hydrogen" refers to hydrogen that does not originate from within the feedstock, such as hydrogen added to the feedstock from an external source. For example, supplemental hydrogen may be added to the system for purposes of increasing the reaction pressure over the hydrogenation catalyst, or to increase the molar ratio of hydrogen to carbon and/or oxygen in order to enhance the production yield of certain reaction product types, such as ketones and alcohols. The supplemental hydrogen may be added at a molar ratio of supplemental hydrogen to APR hydrogen at amounts no greater than 1:1, and preferably no greater than 1:3, and more preferably no greater than 1:10, and still more preferably no greater than 1:20. In the most preferred embodiment, supplemental hydrogen is not added.

The amount of supplemental hydrogen to be added may also be calculated by considering the concentration of oxygenated hydrocarbons in the feedstock solution. Preferably, the amount of supplemental hydrogen added should provide a molar ratio of oxygen atoms in the oxygenated hydrocarbons to moles of hydrogen atoms (i.e., 2 oxygen atoms per molecule of $H_2$ gas) of less than or equal to 1.0. For example, where the feedstock is an aqueous solution consisting of glycerol (3 oxygen atoms), the amount of supplemental hydrogen added to the feedstock is preferably not more than about 1.5 moles of hydrogen gas ($H_2$) per mole of glycerol ($C_3H_8O_3$), and preferably not more than about 1.25, 1.0, 0.75, 0.50 or 0.25. In general, the amount of supplemental hydrogen added is preferably less than 0.75-times, and more preferably not more than 0.67, 0.50, 0.33, 0.30, 0.25, 0.20, 0.15, 0.10, 0.05, 0.01—times the amount of total hydrogen (APR hydrogen and supplemental hydrogen) that would provide a 1:1 atomic ratio of oxygen to hydrogen atoms.

The amount of APR hydrogen within a reactor may be identified or detected by any suitable method. The presence of APR hydrogen is determined based on the composition of the product stream as a function of the composition of the feedstock stream, the catalyst composition(s) and the reaction conditions, independent of the actual reaction mechanism occurring within the feedstock stream. The amount of APR hydrogen may be calculated based on the catalyst, reaction conditions (e.g., flow rate, temperature, pressure) and the contents of the feedstock and the reaction products. For example, the feedstock may be contacted with the APR catalyst (e.g., platinum) to produce APR hydrogen in situ and a first reaction product stream in the absence of a hydrogenation catalyst. The feedstock may also be contacted with both the APR catalyst and the hydrogenation catalyst to produce a second reaction product stream. By comparing the composition of the first reaction product stream and the second reaction product stream at comparable reaction conditions, one may identify the presence of APR hydrogen and calculate the amount of APR hydrogen produced. For example, an increase in the amount of oxygenated compounds with greater degrees of hydrogenation in the reaction product compared to the feedstock components may indicate the presence of APR hydrogen.

Reaction Products

The present invention provides new methods for generating polyols, diols, ketones, aldehydes, carboxylic acids and alcohols in a single catalytic process using in-situ generated hydrogen. The polyols include, without limitation, diols, triols, 1,1,1tris(hydroxymethyl)-ethane (trimethylolethane), sorbitol and mannitol. The diols include, without limitation, ethylene glycol, propylene glycol, butylene glycol, pentylene glycol, hexylene glycol, heptylene glycol, octylene glycol, nonylene glycol and decylene glycol. The triols include, without limitation, glycerol (glycerin), trimethylolpropane, hexanetriol, 2-ethyl-2-(hydroxymethyl)-1,3-propanediol (trimethylolpropane). The ketones include, without limitation, acetone, propan-2-one, 2-oxopropanal, butan-2-one, butane-2,3-dione, 2-hydroxypropanal, 3-hydroxybutan-2-one, pentan-2-one, pentane-2,3-dione, pentane-2,4-dione, hexan-2-one, heptan-2-one, octan-2-one, nonan-2-one, decan-2-one, and isomers thereof. The carboxylic acids include, without limitation, lactic acid, butanoic acid, pentanoic acid, hexanoic acid, heptanoic acid, and isomers and derivatives thereof, including hydroxylated derivatives such as 2-hydroxybutanoic acid. The aldehydes may include, without limitation, acetaldehyde, prionaldehyde, butyraldehyde, pentanal, hexanal, heptanal, octanal, nonal, decanal, and isomers thereof. The alcohols include, without limitation, methanol, ethanol, propyl alcohol, isopropyl alcohol, propanol, butyl alcohol, isobutyl alcohol, butanol, pentanol, hexanol, heptanol.

The specific reaction products produced by the practice of the present invention will depend on various factors, including, without limitation, the feedstock solution, water concentration, reaction temperature, reaction pressure, the reactivity of the catalysts, and the flow rate of the feedstock solution as it affects the space velocity (the mass/volume of reactant per unit of catalyst per unit of time), gas hourly space velocity (GHSV), and weight hourly space velocity (WHSV).

Preferably, the feedstock and reaction stream are contacted with the first catalyst material and the second catalyst material, respectively, at a weight hourly space velocity (WHSV) that is high enough to produce a reaction product comprising one or more oxygenated hydrocarbons. It is believed that decreasing the WHSV below about 0.5 grams of the oxygenated hydrocarbons in the feedstock per hour may increase the amount of hydrocarbons in the reaction products. Therefore, the WHSV is preferably at least about 1.0 grams of the oxygenated hydrocarbons in the feedstock per hour, more preferably the WHSV is about 1.0 to 5.0 g/g hr, including a WHSV of about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4,5, 4.6, 4.7, 4.8, 4.9 and 5.0 g/g hr. In one aspect, the feedstock comprises glycerol contacted with a first catalytic material at a WHSV of about 1.9 or 4.0 g glycerol/hour to produce a reaction product containing propylene glycol.

One skilled in the art will appreciate that varying the factors above, as well as others, will generally result in a modification to the reaction product yield. For example, an increase in flow rate, and thereby a reduction of feedstock exposure to the catalyst over time, will likely result in a decrease in the amount of hydrogen available for hydrogenation over the hydrogenation catalyst. An increase in flow rate may also limit the amount of time for hydrogenation to occur, thereby causing increased yield for higher level diols and polyols, with a reduction in ketone and alcohol yields.

One skilled in the art may also modify the conditions above to enhance the efficiency of the system and improve the costs for manufacturing the desired reaction products. For example, modification of the water to oxygenated hydrocarbon ratio in the feedstock solution may improve the overall thermal efficiency of the process by limiting the need for external temperature controls. The process is thermally efficient if the process is run at feed concentration of greater than 20% by weight oxygenated compound, preferably greater than 30 wt %, more preferably greater than 40 wt % and most preferably greater than 50 wt %.

In one preferred embodiment, the present invention provides a method for producing a polyol from an aqueous feedstock solution comprising glycerol. FIG. 2 shows the reaction schematic for the generation of propylene glycol from glycerol with in-situ hydrogen generation. In the reaction scheme of FIG. 2, a portion of the glycerol is reacted with water under aqueous-phase reforming conditions to generate APR hydrogen and carbon dioxide byproduct (Pathway 1 in FIG. 2). The stoichiometry for Pathway 1 is shown in reaction 5 below:

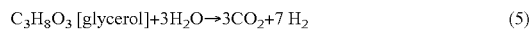
$$C_3H_8O_3 \text{ [glycerol]} + 3H_2O \rightarrow 3CO_2 + 7H_2 \qquad (5)$$

The generated APR hydrogen is then utilized for the dehydration/hydrogenation reaction (Pathway 2 in FIG. 2) for the selective generation of propylene glycol. The stoichiometry for Pathway 2 is shown in reaction 6 below:

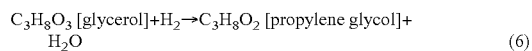
$$C_3H_8O_3 \text{ [glycerol]} + H_2 \rightarrow C_3H_8O_2 \text{ [propylene glycol]} + H_2O \qquad (6)$$

In this step, a portion of the glycerol in the feedstock solution is contacted with a portion of the APR hydrogen over a hydrogenation catalyst under suitable aqueous phase reforming conditions to produce the polyols, such as ethylene glycol and propylene glycol. In the preferred embodiment, the combination of the two reaction pathways occurs according to the overall reaction shown in reaction 7.

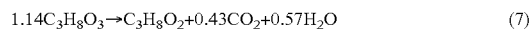
$$1.14 C_3H_8O_3 \rightarrow C_3H_8O_2 + 0.43 CO_2 + 0.57 H_2O \qquad (7)$$

From this theoretical stoichiometry, 0.14 molecules of glycerol must be reformed to generate enough APR hydrogen to hydrogenate one molecule of glycerol to propylene glycol.

In another embodiment, the present invention provides a method for producing an alcohol from an aqueous feedstock solution comprising glycerol. FIG. 3 provides a schematic illustration showing a process for converting glycerol to an alcohol with in-situ hydrogen generation. In this process, glycerol is simultaneously (i.e., Steps 1 and 2 performed concurrently over a single reactor bed) converted to APR hydrogen and an alcohol (and other APR reaction products such carbon monoxide, carbon dioxide, propylene glycol, methane, ethane, propane). The stoichiometry for Pathway 1 is shown in reaction 8 below:

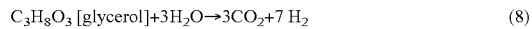
$$C_3H_8O_3 \text{ [glycerol]} + 3H_2O \rightarrow 3CO_2 + 7H_2 \qquad (8)$$

The stoichiometry for Pathway 2 is shown in reaction 9 below:

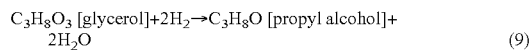
$$C_3H_8O_3 \text{ [glycerol]} + 2H_2 \rightarrow C_3H_8O \text{ [propyl alcohol]} + 2H_2O \qquad (9)$$

The overall reaction stoichiometry to generate 1 molecule of propyl alcohol is shown in reaction 10 below:

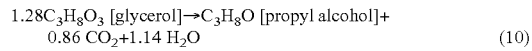
$$1.28 C_3H_8O_3 \text{ [glycerol]} \rightarrow C_3H_8O \text{ [propyl alcohol]} + 0.86 CO_2 + 1.14 H_2O \qquad (10)$$

From this theoretical stoichiometry, 0.28 molecules of glycerol must be reformed to generate enough APR hydrogen to hydrogenate one molecule of glycerol to propyl alcohol.

In yet another embodiment, methods for producing an alcohol from an aqueous feedstock solution comprising sorbitol are provided. FIG. 4 also provides a schematic illustration showing a process for converting sorbitol to an alcohol with in-situ hydrogen generation. In this process, sorbitol is converted simultaneously (i.e., Steps 1 and 2 performed concurrently over a single reactor bed) to hydrogen and an alcohol (and other APR reaction products such as carbon monoxide, carbon dioxide, methane, ethane, propane, butane, pentane, and hexane). The stoichiometry for Pathway 1 is shown in reaction 11 below:

$$C_6H_{14}O_6 \text{ [sorbitol]} + 6H_2O \rightarrow 6CO_2 + 13 H_2 \quad (11)$$

The stoichiometry for Pathway 2 is shown in reaction 12 below:

$$C_6H_{14}O_6 \text{ [sorbitol]} + 5H_2 \rightarrow C_6H_{14}O \text{ [hexanol]} + 5H_2O \quad (12)$$

The overall reaction stoichiometry to generate 1 molecule of hexanol is shown in reaction 13 below:

$$1.38 C_6H_{14}O_6 \text{ [sorbitol]} \rightarrow C_6H_{14}O \text{ [hexanol]} + 2.30 CO_2 + 2.69 H_2O \quad (13)$$

From this theoretical stoichiometry, 0.38 molecules of sorbitol is reformed to generate enough APR hydrogen to hydrogenate one molecule of sorbitol to hexanol.

One preferred method of generating an oxygenated compound comprises the steps of: contacting a first catalytic material comprising one or more Group VIII metals with a first portion of an aqueous feedstock solution comprising water and at least one water soluble oxygenated hydrocarbon having two or more carbon atoms, at: a temperature of about 80° C. to 400° C.; a weight hourly space velocity of at least about 1.0 gram of the oxygenated hydrocarbon per gram of the first catalytic material per hour; and a pressure where the water and the oxygenated hydrocarbons are condensed liquids, to produce aqueous phase reforming (APR) hydrogen; and reacting the APR hydrogen with a second portion of the feedstock solution over a second catalytic material, the second catalytic material different than the first catalytic material and selected from the group consisting of: iron, ruthenium, copper, rhenium, cobalt, nickel, alloys thereof, and mixtures thereof, at: a temperature of about 100° C. to 300° C.; and a pressure of about 200 psig to about 1200 psig, to produce a reaction product comprising one or more oxygenated compounds selected from the group consisting of a polyol, a diol, a ketone, an aldehyde, a carboxylic acid and an alcohol. In one aspect, the first portion of the feedstock solution and/or the second portion of the feedstock solution are contacted with the first catalytic material and the second catalytic material in a reactor vessel at a temperature of about 200° C. to 270° C., including 210° C., 220° C., 230° C., 240° C., 250° C., 260° C. and intervals of 1° C. between 200° C. and 270° C. In another aspect, the second portion of the feedstock solution is contacted with the APR hydrogen and the second catalytic material at a pressure greater than about 365 psig (e.g., 365-1,200 psig), preferably greater than 400 psig (e.g., 478 psig or 400-1,200 psig) or greater than 500 psig (e.g., 585 psig or 500-1,200 psig). The feedstock is preferably passed through a reactor at a weight hourly space velocity (WHSV) selected to provide a product stream comprising one or more oxygenated compounds, including at least one of: a polyol, a ketone, an aldehyde, a carboxylic acid, and an alcohol. For example the WHSV may be about 1.0 to 5.0 grams (including 1.0-4.0, 1.0-3.0, 1.0-2.0, 2.0-5.0, 3.0-5.0, 4.0-5.0 and any other interval of 0.1 therebetween) of the oxygenated hydrocarbon(s) in the feedstock per gram of the catalytic mixture per hour.

Another preferred method of generating propylene glycol comprises the step of contacting a heterogeneous catalyst system comprising one or more Group VIII metals (e.g., one or more metals including platinum) and a hydrogenation catalyst with an aqueous feedstock solution comprising water and a water-soluble oxygenated hydrocarbon (e.g., glycerol or sorbitol) at a temperature and pressure suitable to maintain the feedstock in a liquid phase at (e.g., including temperatures of about 100° C. to 300° C.) at a weight hourly space velocity of at least about 1.0 gram of the water-soluble oxygenated hydrocarbon per gram of the heterogeneous catalyst per hour and a pressure where the feedstock remains a condensed liquid to produce a reaction product comprising one or more oxygenated compounds, such as a polyol (e.g., propylene glycol), an aldehyde, a ketone, a carboxylic acid (e.g., lactic acid) and/or an alcohol. The heterogeneous catalyst system may include a first catalyst material containing a Group VIII metal or any suitable APR catalyst, and a second catalyst containing a hydrogenation catalyst. The heterogeneous catalyst system may be a catalytic mixture of the Group VIII metal and the hydrogenation catalyst. The heterogeneous catalyst system may also be two separate catalytic materials, including an APR catalyst and a hydrogenation catalyst, contacted separately or together with the feedstock. Preferably the heterogeneous catalyst system includes the first catalytic material (e.g., an APR catalyst containing at least one Group VIII metal) and the second catalytic material (e.g., a hydrogenation catalyst) in a molar ratio of 5:1 to 1:5, including ratios of 4:1, 3:1, 2:1, 1:1, 1:2, 1:3, 1:4 and ratio intervals of 0.1 between 5:1 and 1:5.

In certain aspects of the preferred embodiments, the first catalytic material comprises at least one transition metal selected from the group consisting of platinum, nickel, palladium, ruthenium, rhodium, rhenium, iridium, alloys thereof, and mixtures thereof. Alternatively, the first catalytic material may also be selected from one of more of the following groups: platinum, nickel, palladium, ruthenium, rhodium, rhenium, iridium and mixtures thereof; platinum, nickel, palladium, ruthenium, rhodium, rhenium, iridium, and alloys thereof; platinum, nickel, palladium, ruthenium, rhodium, rhenium, iridium, alloys thereof, and mixtures thereof; platinum, nickel, palladium, ruthenium, rhodium, iridium, alloys thereof and mixtures thereof; platinum, nickel, palladium, rhenium, iridium, alloys thereof, and mixtures thereof; nickel, palladium, ruthenium, rhodium, rhenium, iridium, alloys thereof, and mixtures thereof; and nickel, palladium, ruthenium, rhodium, iridium, alloys thereof, and mixtures thereof.

In certain aspects of the preferred embodiments, the second catalytic material is selected from one or more of the following groups: iron, nickel, ruthenium, and cobalt; iron, ruthenium, and cobalt; iron, nickel, and cobalt; iron, nickel, and ruthenium; nickel, ruthenium, and cobalt; iron, nickel and ruthenium; and iron and cobalt. Preferably, the second catalytic material is different from the first catalytic material.

Optionally, the first catalytic material and/or the second catalytic material may be adhered to one or more suitable support materials, such as a support with Bronsted acid sites. The support may comprise carbon. Also optionally, the heterogeneous catalyst may consist essentially of (or consist of) about 5 wt % iron and platinum in a molar ratio of about 1:1 on an activated carbon support; the feedstock may comprise at least about 20 wt % (including 30%, 40%, 50%, 60%, 70%, 80%, 90%, 100%, and amounts of 1% therebetween) of one or more oxygenated hydrocarbon(s) such as glycerol and/or sorbitol; the feedstock may be contacted with the heterogeneous catalyst at a weight hourly space velocity of about 1.0 to 5.0 grams of glycerol per gram of the heterogeneous catalyst per hour and a pressure of about 250-600 psig (including 300-600 psig, 300-1,200 psig, 365-600 psig, 365-1,200 psig, 400-600 psig, 478 psig, 478-1,200 psig, 585 psig and 585-1,200 psig); or the reaction product has a carbon yield of propylene glycol of 40% or greater (including 50%, 60%, 70%, 80%, 90% or greater). The amount of propylene glycol in the reaction product is preferably at least about 5%, 10%, 20%, 30% or 40% of the amount of liquid reaction product.

When present, the amount of supplemental hydrogen is preferably provided sparingly. The feedstock is preferably substantially free of supplemental hydrogen throughout the reaction process. Most preferably, the amount of external supplemental hydrogen is provided in amounts that provide less than one hydrogen atom per oxygen atom in all of the oxygenated hydrocarbons in the feedstock stream prior to contacting a catalyst. For example, the molar ratio between the supplemental hydrogen and the total water-soluble oxygenated hydrocarbons in the feedstock solution is preferably selected to provide no more than one hydrogen atom in the supplemental (external) hydrogen per oxygen atom in the oxygenated hydrocarbon. In generally, the molar ratio of the oxygenated hydrocarbon(s) in the feedstock to the supplemental (external) hydrogen introduced to the feedstock is preferably not more than 1:1, more preferably up to 2:1, 3:1, 5:1, 10:1, 20:1 or greater (including 4:1, 6:1, 7:1, 8:1, 9:1, 11:1, 12:1, 13:1, 14:1, 15:1, 16:1, 17:1, 18:1 and 19:1). The amount (moles) of hydrogen introduced to the feedstock from an external source is preferably 0-30%, 0-25%, 0-20%, 0-15%, 0-10%, 0-5%, 0-2%, 0-1% of the total number of moles of the oxygenated hydrocarbon(s) in the feedstock, including all intervals therebetween. Also preferably, when the feedstock solution or any portion thereof is reacted with APR hydrogen and an external hydrogen, the molar ratio of APR hydrogen to external hydrogen is at least 3:1, including ratios of 5:1, 10:1, 20:1 and ratios therebetween (including 4:1, 6:1, 7:1, 8:1, 9:1, 11:1, 12:1, 13:1, 14:1, 15:1, 16:1, 17:1, 18:1 and 19:1).

In another embodiment, compositions of matter are provided. The composition of matter may be found within a reactor system, including within the reactor vessel and/or within a separator attached thereto. The composition of matter may comprise water, glycerol, carboxylic acid, carbon dioxide, propylene glycol, and a catalyst composition comprising a first catalytic material and a second catalytic material as described above. Preferably, the catalyst composition includes a Group VIII metal and a hydrogen catalyst (e.g., platinum and iron).

In anther embodiment, reactor systems are provided. The reactor system for producing oxygenated compounds from a polyol may include: a first reaction bed adapted to receive an aqueous feedstock solution comprising water and at least one water soluble oxygenated hydrocarbon having two or more carbon atoms, the first reaction bed comprising a first catalyst as described above configured to contact a first portion of the feedstock solution in a condensed phase to form a reactant stream comprising hydrogen; and a second reaction bed configured to receive the reactant stream from the first reaction bed, the second reaction bed comprising a second catalytic material as described above, and configured to cause a reaction between the hydrogen and a second portion of the feedstock solution to produce a product stream comprising one or more oxygenated compounds selected from the group consisting of a polyol (e.g., a diol), a ketone, an aldehyde, a carboxylic acid and an alcohol.

The following examples are included solely to provide a more complete disclosure of the subject invention. Thus, the following examples serve to illuminate the nature of the invention, but do not limit the scope of the invention disclosed and claimed herein in any fashion.

EXAMPLES

Example 1

Illustrative Reactor System 1

Figure 5:
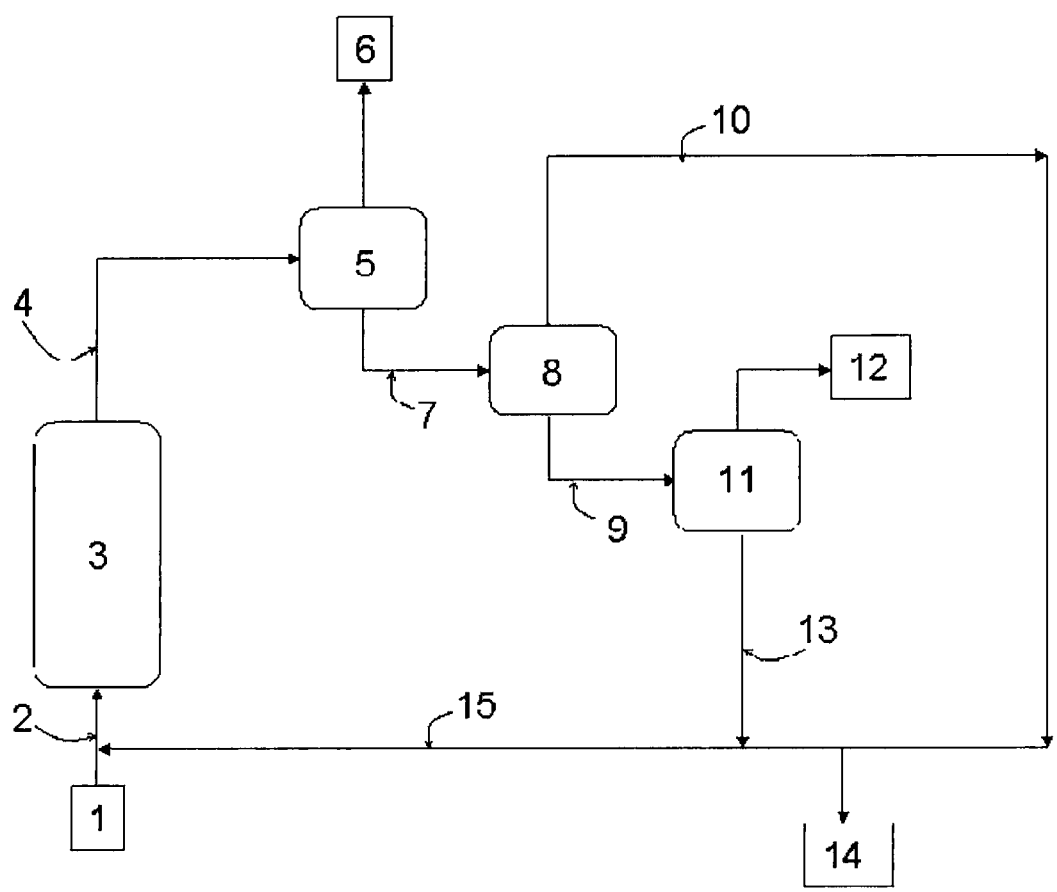
FIG. 5 is a schematic diagram illustrating a process for converting a polyol to a diol or alcohol using in-situ generated hydrogen.

FIG. 5 is a schematic illustration showing one preferred process for converting a feedstock solution 1 to a final desired product 12 using a single reactor containing a catalyst composed of a mixture of the APR catalyst and hydrogenation catalyst. The feedstock solution 1 includes water combined with one or more oxygenated hydrocarbons, such as glycerol or sugar alcohol. The feedstock solution 1 is combined with a recycle stream 15 containing unreacted polyols, water, and byproducts of the process, such as methanol and ethanol, from the process. The combined stream 2 is fed via an HPLC pump (not shown) to reactor system 3 having the APR/hydrogenation catalyst, where a portion of the stream reacts with water over the catalyst to form APR hydrogen, which subsequently reacts with the other portion of the stream over the hydrogenation catalyst to generate the desired products.

The effluent stream 4 from the reactor 3 contains a mixture of water, hydrogen, carbon dioxide, light hydrocarbons, light alcohols (methanol and ethanol), diol product and unreacted glycerol. The mixture is cooled and separated in a two-phase separator 5 where the non-condensed gases (such as hydrogen, carbon dioxide, methane, ethane and propane) are removed via stream 6 from the phase containing the water soluble alcohols and diols. The non-condensable stream 6 can be either combusted to create process heat (i.e., heat for driving the reaction in reactor 3) or sent to a separation system where hydrogen can be recovered for recycle back to stream 2. The aqueous stream 7 may be sent to a separator 8 where the light alcohols (methanol and ethanol) and water are removed and recycled back via stream 10 to the reactor inlet. A purge stream 14 is included to prevent a build-up of water in the reactor system.

A crude product stream 9, containing unreacted glycerol and desired polyol, diol, ketone, aldehyde, carboxylic acid and/or alcohol products, is recovered from separator 8 via stream 9 and sent to a finishing separator where the desired product 12 is separated from unreacted glycerol 13. The unreacted glycerol stream is then added to stream 10 and recycled back to the reactor system via stream 15.

Example 2

Illustrative Reactor System 2

Figure 6:
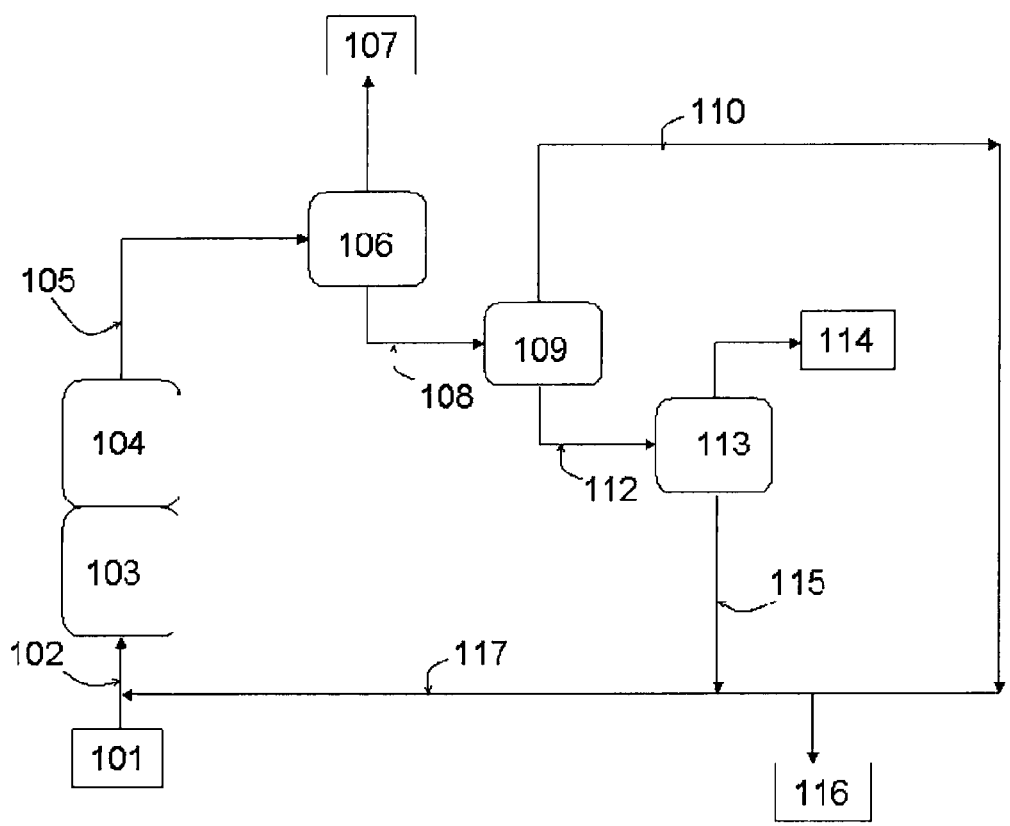
FIG. 6 is a schematic diagram illustrating a process for generating reaction products from a polyol using a reactor having a first reaction chamber for generating hydrogen and a second hydrogenation chamber.

FIG. 6 is a schematic showing another preferred process for converting a polyol feedstock solution 101 to a final diol product 114 using a reactor system that includes a first reactor bed 103 having an APR catalyst and a second reactor bed 104 having a hydrogenation catalyst. The feedstock solution 101 includes water combined with one or more oxygenated hydrocarbons, such as sugar alcohol or glycerol. Feedstock solution 101 is combined with a recycle stream 117 containing unreacted polyols, water, and underdesirable byproducts (e.g., methanol and ethanol). The combined stream 102 is fed via an HPLC pump (not shown) to first reactor bed 103 where a portion of the stream reacts with water over the APR catalyst to form APR hydrogen. The recycled alcohols (methanol and ethanol) also react with water over the APR catalyst to form APR hydrogen and light hydrocarbons, such as methane and ethane.

Effluent containing APR hydrogen, water, $CO_2$, light hydrocarbons and polyols move from first reactor bed 103 to second reactor bed 104 where the APR hydrogen reacts with a portion of the polyols to generate the desired products. In this illustration, the reactor bed 103 and reactor bed 104 are set in an up-flow orientation to allow the generated APR hydrogen to percolate from reactor bed 103 through second reactor bed 104 to maximize the interaction of APR hydrogen and stream 102 over the hydrogenation catalyst. Reactor beds 103 and 104 may also be designed to accommodate downflow or horizontal-flow orientations.

The effluent stream 105 from the reactor system contains a mixture of water, hydrogen, carbon dioxide, light hydrocarbons, light alcohols (methanol and ethanol), diol and polyol products, and unreacted glycerol. The mixture is cooled and separated in a two-phase separator 106 where the non-condensable gases (such as hydrogen, carbon dioxide, methane, ethane and propane) are removed via stream 107 from the phase containing the water soluble alcohols, diols and polyols. The non-condensable stream 107 can be either combusted to create process heat or sent to a separation system where hydrogen is recovered for possible recycle back to stream 102. The aqueous stream 108 is sent to a separator 109 where the light alcohols (methanol and ethanol) and water are removed and recycled back via stream 110 to the reactor inlet. A purge stream 116 is included to prevent a build-up of water in the reactor system.

A crude product stream 112, containing unreacted glycerol and the desired polyol, diol and/or alcohol products, is recovered from separator 109 via stream 112 and sent to a finishing separator 113 where the desired product 114 is separated from unreacted glycerol 115. The unreacted glycerol stream is added to stream 110 and recycled back to the reactor system via stream 117.

Example 3

Illustrative Reactor System 3

Figure 7:
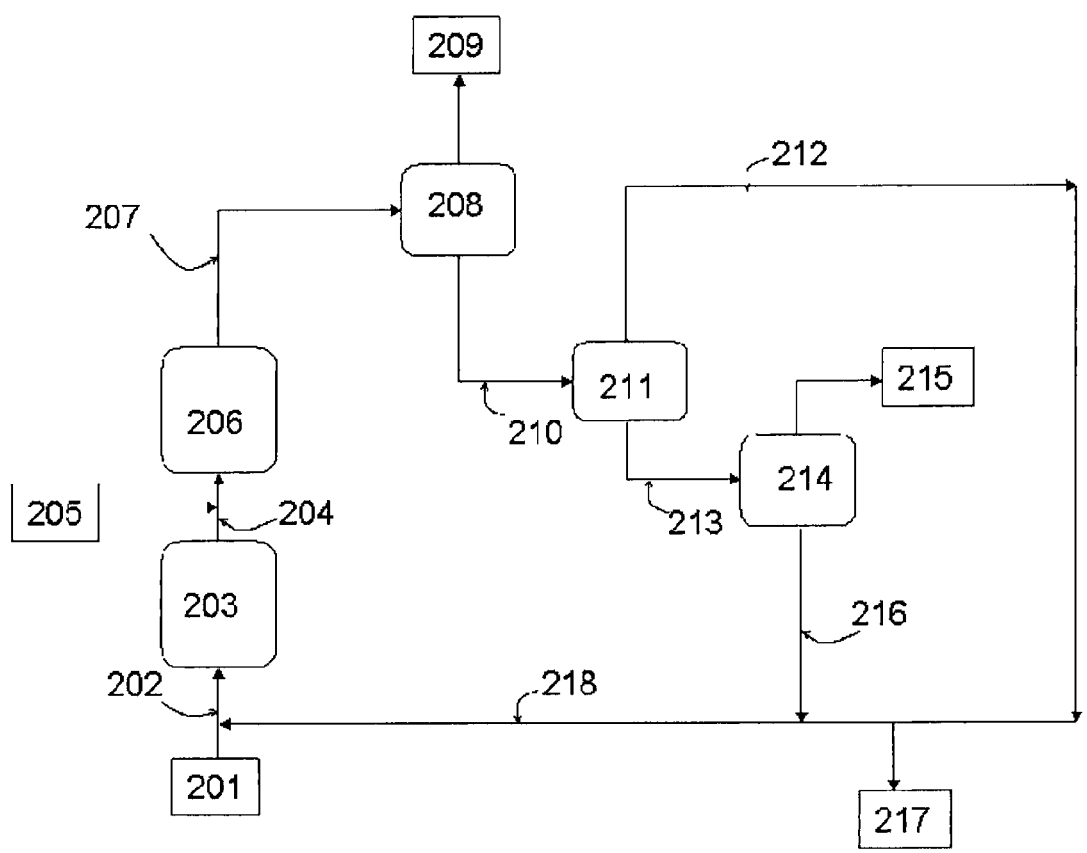
FIG. 7 is a schematic diagram illustrating a process for generating reaction products from a polyol with an added supplement using a reactor having a first reaction chamber for generating hydrogen and a second hydrogenation chamber.

FIG. 7 is a schematic showing another preferred process for converting a feedstock solution 201 to a final product 215 with the introduction of a supplement 205. Supplement 205 may include various salts, acids, additional feedstock solution, hydrogen or byproducts of the process.

Feedstock solution 201 includes water combined with one or more oxygenated hydrocarbons, such as glycerol or sugar alcohol. Feedstock solution 201 may contain the same combination as feedstock solution 205 or a combination of one or more low cost oxygenated compounds, such as waste methanol from a biodiesel process, ethylene glycol from spent antifreeze, or low cost alcohols. Stream 201 may also be combined with recycle stream 218, which contains unreacted polyols, water and underdesirable byproducts, such as methanol and ethanol, to form combined stream 202.

Combined stream 202 is fed via an HPLC pump (not shown) to reactor bed 203 having an APR catalyst. Oxygenated hydrocarbons in combined stream 202 react with water over the APR catalyst to form APR hydrogen, while the recycled alcohols (i.e., methanol and ethanol) form hydrogen and light hydrocarbons, such as methane and ethane.

Effluent from first reactor bed 204, containing APR hydrogen, water, $CO_2$, light hydrocarbons, and unreacted hydrocarbons, is combined with supplement 205. In this illustration, supplement 205 is a feedstock solution containing a higher grade of oxygenated hydrocarbons, such as purified glycerol. The combined effluent 204 and supplement 205 are directed to reactor bed 206 that includes a hydrogenation catalyst for reacting the APR hydrogen with the oxygenated hydrocarbons to generate the desired polyol, diol and/or alcohol product 215. Effluent stream 207 from the reactor contains a mixture of water, hydrogen, carbon dioxide, light hydrocarbons, light alcohols (methanol and ethanol), polyols, diols, ketones, aldehydes, carboxylic acids and unreacted glycerol.

The mixture is cooled and separated in a two-phase separator 208 where the non-condensable gases, such as hydrogen, carbon dioxide, methane, ethane and propane, are removed via stream 209 from the phase containing water-soluble polyols, alcohols and/or diols. The stream 209 can be either combusted to create process heat or sent to a separation system where hydrogen can be recovered for possible recycle back to stream 201 or used as a supplement 205.

Aqueous stream 210 is sent to a separator 211 where the light alcohols (methanol and ethanol) and water are removed and recycled back via stream 212 to the reactor inlet. A purge stream 217 is included to prevent a build-up of water in the reactor system. A crude product stream 213 containing the desired product 215 and unreacted hydrocarbons is recovered from separator 211 via stream 213 and sent to a finishing separator 214 where the desired product 215 is separated from the unreacted hydrocarbons 216. The unreacted hydrocarbon stream is added to stream 216 and recycled back to the reactor system via stream 218 or used as supplement 205.

Example 4

Illustrative Reactor System 4

Figure 8:
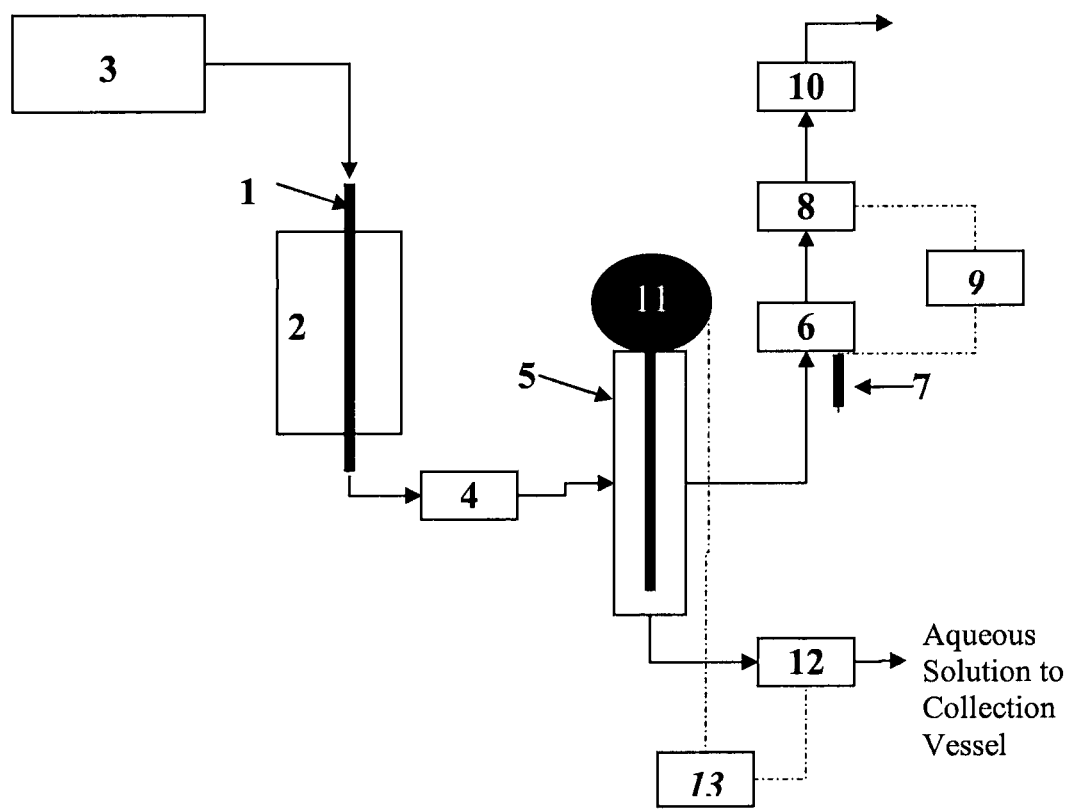
FIG. 8 is a schematic diagram of a reactor system that can be used to evaluate the generation of polyols from glycerol via aqueous-phase reforming.

The generation of polyols from glycerol is performed using the test system illustrated in FIG. 8. The reactor in the system is configured in a down flow orientation which improves contact of the aqueous feedstock solutions with in-situ generated APR hydrogen as it flows through the reactor.

Catalysts are loaded into a stainless steel tube reactor 1, which is installed in an aluminum block heater 2 to maintain isothermal conditions. The reaction temperature is controlled by the temperature control subsystem. Some components of the temperature control subsystem (not shown in FIG. 8) include a thermocouple inserted into the tube reactor, resistive heaters mounted on the aluminum block, and a PID controller.

Substrate solutions (i.e., feedstock solutions) can be selected to be continuously fed into the reactor using an HPLC pump 3. The material exiting the reactor is cooled as it passes through heat exchanger 4 before entering the phase separator 5.

Gasses exit the phase separator via the gas manifold 6, which is maintained at constant pressure by the pressure control subsystem. Components of the pressure control subsystem include: the pressure sensor 7, pressure control valve 8, and PID controller 9. The quantity of gas released by the pressure control valve 8 is measured by mass flow meter 10. The composition of this gas is monitored by gas chromatography.

The liquid level in phase separator 5 is maintained at constant level by the level control subsystem. The components of the level control subsystem include the level sensor 11 in the phase separator, a level control valve 12 and PID controller 13. The aqueous solution drained from the phase separator during a catalyst evaluation experiment is collected and the quantity collected measured gravimetrically. Analysis of this solution may include, pH, total organic carbon concentration, GC to determine the concentrations of unreacted substrate and specific intermediates and side products.

Example 5

Preparation of Improved Carbon Support

Hydrogen peroxide was used to functionalize activated carbons to provide improved supports for catalysts. See S. R. de Miguel, O. A. Scelza, M. C. Roman-Martinez, C. Salinas Martinez de Lecea, D. Cazorla-Amoros, A. Linares-Solano, Applied Catalysis A: General 170 (1998) 93. Activated carbon, 61 g, was added slowly to 1600 ml of 30% hydrogen peroxide solution. After the addition of carbon was complete, the mixture was left overnight. The aqueous phase was decanted and the carbon washed three times with 1600 mL of DI water, then dried under vacuum at 100° C.

Example 6

Preparation of a Bimetallic Catalyst System

A bimetallic catalyst system containing a 5 wt % platinum (APR catalyst) and iron (hydrogenation catalyst) mixture (molar ratio 1:1) supported on activated carbon was prepared using incipient wetness techniques. An aqueous solution, with a volume equal to incipient wetness volume for the carbon to be impregnated, 10.4 mL, and containing 1.72 g of dihydrogen hexachloroplatinate (IV) hexahydrate (Alfa Aesar, 39.85% Pt) and 1.42 g of iron(III) nitrate nonahydrate (Alfa Aesar) was applied dropwise, while stirring, to 13.02 g of hydrogen peroxide functionalized carbon (Example 5). The wetted carbon was dried at 100° C. under vacuum.

Example 7

Propylene Glycol Production

The catalyst system described in Example 6 was tested in the apparatus described in Example 4 using a feedstock solution containing 50 wt % glycerol. Prior to introducing the glycerol feedstock solution, the catalyst was treated under flowing hydrogen at 350° C. The reaction conditions were set at 240° C., 33.0 bar (478 psig), and WHSV of 4.0 grams glycerol per gram of catalyst per hour. The glycerol conversion was 64%. This experiment was repeated with a second feedstock solution containing 50 wt % glycerol and 50% water feed over the catalyst of Example 6 the following reaction conditions: 260° C., 40.3 bar (585 psig), WHSV of 1.9 grams glycerol per gram of catalyst per hour.

Figure 9:
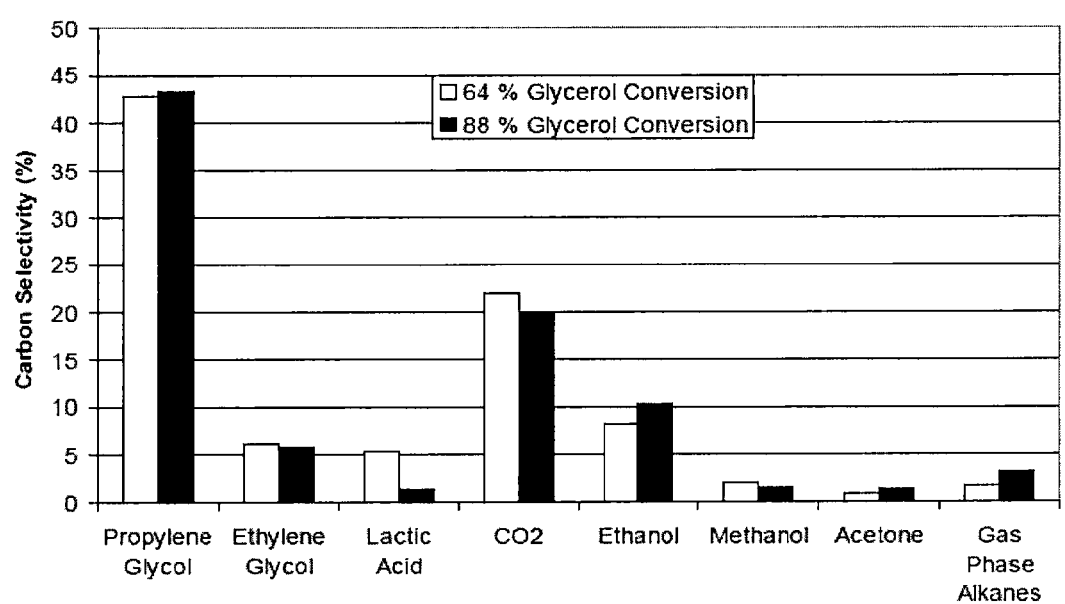
FIG. 9 is a graph depicting the distribution of carbon products during aqueous phase reforming of glycerol over a modified platinum catalyst.

At the low temperature regime, pressures and catalyst amounts used were all commercially viable conditions for the APR process. The glycerol conversions for these two cases were 64% and 88% of the theoretical maximum, respectively. FIG. 9 summarizes the yield of carbon containing products, and shows the selectivity of the conversion of glycerol to the carbon-containing products for the high and low temperature reactions. The graph shows that propylene glycol was the major product generated, followed by carbon dioxide (a byproduct of the in-situ generation of APR hydrogen), ethanol, and ethylene glycol. The gas phase alkanes included methane, ethane, and propane, with methane being the most abundant gas-phase alkane.

The results confirm that it is possible to generate propylene glycol in reasonable yields via liquid-phase reforming of aqueous solutions of glycerol, and that it is possible to generate significant or predominant amounts of propylene glycol from glycerol with in-situ generated hydrogen and, preferably, without concurrently introducing hydrogen from an external source. The presence of byproducts from the hydrogen generation process surprisingly did not significantly impact the ability of the glycerol conversion to propylene glycol and other products.

The described embodiments and examples are to be considered in all respects only as illustrative and not restrictive, and the scope of the invention is, therefore, indicated by the appended claims rather than by the foregoing description. All changes which come within the meaning and range of equivalency of the claims are to be embraced within their scope.

I claim:

1. A method of generating ketones or alcohols, the method comprising the steps of:
    a. contacting a first catalytic material comprising one or more Group VIII metals with a first portion of an aqueous feedstock solution comprising water and at least one water-soluble oxygenated hydrocarbon having two or more carbon atoms under conditions sufficient to produce hydrogen; and
    b. reacting the hydrogen with a second portion of the aqueous feedstock solution over a second catalytic material, the second catalytic material different than the first catalytic material and comprising iron, ruthenium, copper, rhenium, cobalt, nickel, an alloy of at least two of the foregoing, or mixtures of at least two of the foregoing, under conditions sufficient to produce one or more ketones selected from the group consisting of acetone, propanone, butanone, pentanone, and hexanone, or one or more alcohols selected from the group consisting of methanol, ethanol, iso-propyl alcohol, propanol, butanol, pentanol, and hexanol.

2. The method of claim 1 further comprising the step of adding a supplemental hydrogen to react with at least a portion of the second portion of the aqueous feedstock solution.

3. The method of claim 1, wherein the first catalytic material contacts the first portion of the aqueous feedstock at:
    a. a temperature of about 80° C. to 400° C.; and
    b. a pressure where at least a portion of the water and the oxygenated hydrocarbons are condensed liquids.

4. The method of claim 1, wherein the hydrogen reacts with a second portion of the feedstock solution at:
    a. a temperature of about 100° C. to 300° C.; and
    b. a pressure of about 72 psig to about 1300 psig.

5. The method of claim 1, wherein the second portion of the feedstock solution further comprises oxygenated hydrocarbons formed by contacting the feedstock solution with the first catalytic material.

6. The method of claim 1, wherein the second portion of the feedstock solution is contacted with the hydrogen and second catalytic material at a pressure greater than about 365 psig.

7. The method of claim 1, wherein the molar ratio of the first catalytic material to the second catalytic material is about 5:1 to 1:5.

8. The method of claim 1, wherein the first catalytic material comprises at least one transition metal selected from the group consisting of platinum, nickel, palladium, ruthenium, rhodium, rhenium, iridium, an alloy of at least two of the foregoing, and mixtures of at least two of the foregoing.

9. The method of claim 1, wherein the second catalytic material is selected from the group consisting of iron, nickel, rhenium, ruthenium, and cobalt.

10. The method of claim 1, wherein the first catalytic material and the second catalytic material are combined in a catalytic mixture.

11. The method of claim 10, wherein the first catalytic material comprises at least one transition metal selected from the group consisting of: platinum, nickel, palladium, ruthenium, rhodium, rhenium, iridium, an alloy of at least two of the foregoing and mixtures of at least two of the foregoing; and the second catalytic metal is iron or rhenium.

12. The method of claim 11, wherein the first catalytic material is platinum and the second catalytic material is rhenium.

13. The method of claim 10, wherein the first portion of the feedstock solution and the second portion of the feedstock solution are contacted with the first catalytic material and the second catalytic material in a reactor vessel at a temperature of about 200° C. to 270° C.

14. The method of claim 10, wherein the catalytic mixture is adhered to a support.

15. The method of claim 14, wherein the support is selected from the group consisting of carbon, silica, silica-alumina, alumina, zirconia, titania, ceria, vanadia, and mixtures thereof.

16. The method of claim 15, wherein the support is an activated carbon.

17. The method of claim 15, wherein the support comprises zirconia.

18. The method of claim 1, wherein the first portion of the feedstock solution is contacted with the first catalytic material at a temperature of about 150° C. to 270° C. and the second portion of the feedstock solution is contacted with the second catalytic material at a temperature of about 200° C. to 270° C.

19. A method of generating ketones or alcohols, the method comprising the steps of:
   a. contacting a first catalytic material comprising one or more Group VIII metals with a first portion of an aqueous feedstock solution comprising water, a recycle stream and at least one water-soluble oxygenated hydrocarbon having two or more carbon atoms under conditions sufficient to produce hydrogen; and
   b. reacting the hydrogen with a second portion of the aqueous feedstock solution over a second catalytic material, the second catalytic material different than the first catalytic material and selected from the group consisting of: iron, ruthenium, copper, rhenium, cobalt, nickel, an alloy of at least two of the foregoing, and mixtures of at least two of the foregoing, under conditions sufficient to produce an effluent stream comprising unreacted oxygenated hydrocarbons, byproducts and one or more ketones selected from the group consisting of acetone, propanone, butanone, pentanone, and hexanone, or one or more alcohols selected from the group consisting of methanol, ethanol, iso-propyl alcohol, propanol, butanol, pentanol, and hexanol; and
   c. separating at least a portion of the unreacted oxygenated hydrocarbons and byproducts from the effluent stream into the recycle stream; and
   d. mixing at least a portion of the recycle stream with one or more water-soluble oxygenated hydrocarbons to provide the aqueous feedstock solution.

20. The method of claim 19 further comprising the step of adding a supplemental hydrogen to react with at least a portion of the second portion of the aqueous feedstock solution.

21. The method of claim 19, wherein the first catalytic material contacts the first portion of the aqueous feedstock at:
   a. a temperature of about 80° C. to 400° C.; and
   b. a pressure where at least a portion of the water and the oxygenated hydrocarbons are condensed liquids.

22. The method of claim 19, wherein the hydrogen reacts with a second portion of the feedstock solution at:
   a. a temperature of about 100° C. to 300° C.; and
   b. a pressure of about 72 psig to about 1300 psig.

23. The method of claim 19, wherein the second portion of the feedstock solution is contacted with the hydrogen and the second catalytic material at a pressure greater than about 365 psig.

24. The method of claim 19, wherein the molar ratio of the first catalytic material to the second catalytic material is about 5:1 to 1:5.

25. The method of claim 19, wherein the first catalytic material comprises at least one transition metal selected from the group consisting of platinum, nickel, palladium, ruthenium, rhodium, rhenium, iridium, an alloy of at least two of the foregoing, and mixtures of at least two of the foregoing.

26. The method of claim 19, wherein the second catalytic material is selected from the group consisting of iron, nickel, rhenium, ruthenium, and cobalt.

27. The method of claim 19, wherein the first catalytic material and the second catalytic material are combined in a catalytic mixture.

28. The method of claim 27, wherein the first catalytic material comprises at least one transition metal selected from the group consisting of: platinum, nickel, palladium, ruthenium, rhodium, rhenium, iridium, an alloy of at least two of the foregoing and mixtures of at least two of the foregoing; and the second catalytic metal is iron or rhenium.

29. The method of claim 27, wherein the first catalytic material is platinum and the second catalytic material is rhenium.

30. The method of claim 27, wherein the first catalytic material and the second catalytic material are adhered to a support.

31. The method of claim 30, wherein the support is selected from the group consisting of carbon, silica, silica-alumina, alumina, zirconia, titania, ceria, vanadia, and mixtures thereof.

32. The method of claim 31, wherein the support is an activated carbon.

33. The method of claim 31, wherein the support comprises zirconia.

34. The method of claim 19, wherein the first portion of the feedstock solution is contacted with the first catalytic material at a temperature of about 150° C. to 270° C. and the second portion of the feedstock solution is contacted with the second catalytic material at a temperature of about 200° C. to 270° C.

35. A method of generating ketones or alcohols, the method comprising the steps of:
   a. contacting a first catalytic material comprising one or more Group VIII metals with a first portion of an aqueous feedstock solution comprising water and at least one water-soluble oxygenated hydrocarbon having two or more carbon atoms under conditions sufficient to produce aqueous phase reforming (APR) hydrogen; and
   b. reacting the APR hydrogen and a supplemental hydrogen with a second portion of the aqueous feedstock solution over a second catalytic material, the second catalytic material different than the first catalytic material and comprising iron, ruthenium, copper, rhenium, cobalt, nickel, an alloy of at least two of the foregoing, or mixtures of at least two of the foregoing, under conditions sufficient to produce one or more ketones selected from the group consisting of acetone, propanone, butanone, pentanone, and hexanone, or one or more alcohols selected from the group consisting of methanol, ethanol, iso-propyl alcohol, propanol, butanol, pentanol, and hexanol.

36. The method of claim 35, wherein the first catalytic material contacts the first portion of the aqueous feedstock at:
   a. a temperature of about 80° C. to 400° C.; and
   b. a pressure where at least a portion of the water and the oxygenated hydrocarbons are condensed liquids.

37. The method of claim 35, wherein the APR hydrogen and the supplemental hydrogen react with a second portion of the feedstock solution at:
   a. a temperature of about 100° C. to 300° C.; and
   b. a pressure of about 72 psig to about 1300 psig.

38. The method of claim 35, wherein the second portion of the feedstock solution is contacted with the APR hydrogen, the supplemental hydrogen and the second catalytic material at a pressure greater than about 365 psig.

39. The method of claim 35, wherein the molar ratio of the first catalytic material to the second catalytic material is about 5:1 to 1:5.

40. The method of claim 35, wherein the first catalytic material comprises at least one transition metal selected from the group consisting of platinum, nickel, palladium, ruthenium, rhodium, rhenium, iridium, an alloy of at least two of the foregoing, and mixtures of at least two of the foregoing.

41. The method of claim 35, wherein the second catalytic material is selected from the group consisting of iron, nickel, rhenium, ruthenium, and cobalt.

42. The method of claim 35, wherein the first catalytic material and the second catalytic material are combined in a catalytic mixture.

43. The method of claim 42, wherein the first catalytic material and second catalytic material are adhered to a support.

44. The method of claim 43, wherein the support is selected from the group consisting of carbon, silica, silica-alumina, alumina, zirconia, titania, ceria, vanadia, and mixtures thereof.

* * * * *